（12）United States Patent
Prabhu

(10) Patent No.: US 11,653,947 B2
(45) Date of Patent: May 23, 2023

(54) CARDIAC VALVE CUTTING DEVICE

(71) Applicant: Evalve, Inc., Santa Clara, CA (US)

(72) Inventor: Santosh V. Prabhu, Sunnyvale, CA (US)

(73) Assignee: EVALVE, INC., Santa Clara, CA (US)

( * ) Notice: Subject to any disclaimer, the term of this patent is extended or adjusted under 35 U.S.C. 154(b) by 125 days.

(21) Appl. No.: 17/382,606

(22) Filed: Jul. 22, 2021

(65) Prior Publication Data
US 2022/0008096 A1 Jan. 13, 2022

Related U.S. Application Data

(62) Division of application No. 15/724,545, filed on Oct. 4, 2017, now Pat. No. 11,071,564.
(Continued)

(51) Int. Cl.
A61B 17/3207 (2006.01)
A61B 18/24 (2006.01)
(Continued)

(52) U.S. Cl.
CPC .. *A61B 17/320758* (2013.01); *A61B 17/3201* (2013.01); *A61B 17/32056* (2013.01); *A61B 17/320725* (2013.01); *A61B 17/320783* (2013.01); *A61B 18/1492* (2013.01); *A61B 18/24* (2013.01); *A61B 2017/00243* (2013.01); *A61B 2017/00287* (2013.01); *A61B 2017/00323* (2013.01); *A61B 2017/00349* (2013.01); *A61B 2017/00353* (2013.01); *A61B 2017/00398* (2013.01); *A61B 2017/00411* (2013.01);
(Continued)

(58) Field of Classification Search
CPC .... A61B 17/320758; A61B 17/320725; A61B 17/320783; A61B 18/1492; A61B 18/24
See application file for complete search history.

(56) References Cited

U.S. PATENT DOCUMENTS

| 1,996,261 A | 4/1935 | Storz |
| 2,097,018 A | 10/1937 | Chamberlin |

(Continued)

FOREIGN PATENT DOCUMENTS

| CN | 1469724 A | 1/2004 |
| CN | 102770080 A | 11/2012 |

(Continued)

OTHER PUBLICATIONS

Office Action received for U.S. Appl. No. 15/423,060, dated Oct. 28, 2019.
(Continued)

*Primary Examiner* — Phong Son H Dang
(74) *Attorney, Agent, or Firm* — Workman Nydegger

(57) ABSTRACT

An interventional device for cutting tissue at a targeted cardiac valve, such as a mitral valve. The interventional device includes a catheter having a proximal end and a distal end. A cutting mechanism is positionable at the distal end, such as by routing the cutting mechanism through the catheter to position it at the distal end. The cutting mechanism includes one or more cutting elements configured for cutting valve tissue when engaged against the tissue. A handle is coupled to the proximal end of the catheter and includes one or more controls for actuating the cutting mechanism.

10 Claims, 10 Drawing Sheets

Related U.S. Application Data

(60) Provisional application No. 62/404,558, filed on Oct. 5, 2016.

(51) Int. Cl.

| | |
|---|---|
| *A61B 18/14* | (2006.01) |
| *A61B 17/3201* | (2006.01) |
| *A61B 17/3205* | (2006.01) |
| *A61B 17/22* | (2006.01) |
| *A61F 2/24* | (2006.01) |
| *A61B 17/00* | (2006.01) |
| *A61B 17/32* | (2006.01) |
| *A61B 18/00* | (2006.01) |

(52) U.S. Cl.
CPC ............ *A61B 2017/00477* (2013.01); *A61B 2017/00783* (2013.01); *A61B 2017/00876* (2013.01); *A61B 2017/22071* (2013.01); *A61B 2017/320028* (2013.01); *A61B 2017/320064* (2013.01); *A61B 2018/00184* (2013.01); *A61B 2018/00369* (2013.01); *A61B 2018/00601* (2013.01); *A61B 2018/00922* (2013.01); *A61B 2018/146* (2013.01); *A61B 2018/1475* (2013.01); *A61F 2/2412* (2013.01)

(56) References Cited

U.S. PATENT DOCUMENTS

| | | |
|---|---|---|
| 2,108,206 A | 2/1938 | Mecker |
| 3,296,668 A | 1/1967 | Aiken |
| 3,378,010 A | 4/1968 | Codling et al. |
| 3,470,875 A | 10/1969 | Johnson |
| 3,557,780 A | 1/1971 | Sato |
| 3,671,979 A | 6/1972 | Moulopoulos |
| 3,675,639 A | 7/1972 | Cimber |
| 3,874,338 A | 4/1975 | Happel |
| 3,874,388 A | 4/1975 | King et al. |
| 4,007,743 A | 2/1977 | Blake |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,312,337 A | 1/1982 | Donohue |
| 4,425,908 A | 1/1984 | Simon |
| 4,458,682 A | 7/1984 | Cerwin |
| 4,484,579 A | 11/1984 | Meno et al. |
| 4,487,205 A | 12/1984 | Di et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,872,455 A | 10/1989 | Pinchuk et al. |
| 4,878,495 A | 11/1989 | Grayzel |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox et al. |
| 5,042,707 A | 8/1991 | Taheri |
| 5,047,041 A | 9/1991 | Samuels |
| 5,049,153 A | 9/1991 | Nakao et al. |
| 5,053,043 A | 10/1991 | Gottesman et al. |
| 5,061,277 A | 10/1991 | Carpentier et al. |
| 5,069,679 A | 12/1991 | Taheri |
| 5,071,428 A | 12/1991 | Chin et al. |
| 5,078,722 A | 1/1992 | Stevens |
| 5,078,723 A | 1/1992 | Dance et al. |
| 5,108,368 A | 4/1992 | Hammerslag et al. |
| 5,125,758 A | 6/1992 | Dewan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,217,460 A | 6/1993 | Knoepfler |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,336,227 A | 8/1994 | Nakao et al. |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Krauter et al. |
| 5,368,564 A | 11/1994 | Savage |
| 5,368,601 A | 11/1994 | Sauer et al. |
| 5,383,886 A | 1/1995 | Kensey et al. |
| 5,387,219 A | 2/1995 | Rappe |
| 5,391,182 A | 2/1995 | Chin |
| 5,403,312 A | 4/1995 | Yates et al. |
| 5,403,326 A | 4/1995 | Harrison et al. |
| 5,411,552 A | 5/1995 | Andersen et al. |
| 5,417,684 A * | 5/1995 | Jackson ........... A61B 17/32056 606/1 |
| 5,417,699 A | 5/1995 | Klein et al. |
| 5,417,700 A | 5/1995 | Egan |
| 5,423,830 A | 6/1995 | Schneebaum et al. |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,472,423 A | 12/1995 | Gronauer |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |

(56) References Cited

U.S. PATENT DOCUMENTS

| | | | |
|---|---|---|---|
| 5,562,678 A | 10/1996 | Booker | |
| 5,569,274 A | 10/1996 | Rapacki et al. | |
| 5,571,085 A | 11/1996 | Accisano, III | |
| 5,571,137 A | 11/1996 | Marlow et al. | |
| 5,571,215 A | 11/1996 | Sterman et al. | |
| 5,575,802 A | 11/1996 | McQuilkin et al. | |
| 5,582,611 A | 12/1996 | Tsuruta et al. | |
| 5,584,803 A | 12/1996 | Stevens et al. | |
| 5,593,424 A | 1/1997 | Northrup, III | |
| 5,593,435 A | 1/1997 | Carpentier et al. | |
| 5,609,598 A | 3/1997 | Laufer et al. | |
| 5,617,854 A | 4/1997 | Munsif | |
| 5,618,306 A | 4/1997 | Roth et al. | |
| 5,620,452 A | 4/1997 | Yoon | |
| 5,620,461 A | 4/1997 | Muijs et al. | |
| 5,626,588 A | 5/1997 | Sauer et al. | |
| 5,634,932 A | 6/1997 | Schmidt | |
| 5,636,634 A | 6/1997 | Kordis et al. | |
| 5,639,277 A | 6/1997 | Mariant et al. | |
| 5,640,955 A | 6/1997 | Ockuly et al. | |
| 5,649,937 A | 7/1997 | Bito et al. | |
| 5,662,681 A | 9/1997 | Nash et al. | |
| 5,669,917 A | 9/1997 | Sauer et al. | |
| 5,669,919 A | 9/1997 | Sanders et al. | |
| 5,690,671 A | 11/1997 | McGurk et al. | |
| 5,695,504 A | 12/1997 | Gifford et al. | |
| 5,695,505 A | 12/1997 | Yoon | |
| 5,702,825 A | 12/1997 | Keita et al. | |
| 5,706,824 A | 1/1998 | Whittier | |
| 5,709,707 A | 1/1998 | Lock et al. | |
| 5,713,910 A | 2/1998 | Gordon et al. | |
| 5,713,911 A | 2/1998 | Racenet et al. | |
| 5,715,817 A | 2/1998 | Stevens-Wright et al. | |
| 5,716,367 A | 2/1998 | Koike et al. | |
| 5,718,725 A | 2/1998 | Sterman et al. | |
| 5,719,725 A | 2/1998 | Nakao | |
| 5,722,421 A | 3/1998 | Francese et al. | |
| 5,725,542 A | 3/1998 | Yoon | |
| 5,725,556 A | 3/1998 | Moser et al. | |
| 5,738,649 A | 4/1998 | Macoviak | |
| 5,741,271 A * | 4/1998 | Nakao | A61B 18/24 |
| | | | 604/523 |
| 5,741,280 A | 4/1998 | Fleenor | |
| 5,746,747 A * | 5/1998 | McKeating | A61B 17/221 |
| | | | 606/113 |
| 5,749,828 A | 5/1998 | Yeung | |
| 5,759,193 A | 6/1998 | Burbank et al. | |
| 5,769,812 A | 6/1998 | Stevens et al. | |
| 5,769,863 A | 6/1998 | Garrison | |
| 5,772,578 A | 6/1998 | Heimberger et al. | |
| 5,782,845 A | 7/1998 | Shewchuk | |
| 5,797,927 A | 8/1998 | Yoon | |
| 5,797,960 A | 8/1998 | Stevens et al. | |
| 5,810,847 A | 9/1998 | Laufer et al. | |
| 5,810,849 A | 9/1998 | Kontos | |
| 5,810,853 A | 9/1998 | Yoon | |
| 5,810,876 A | 9/1998 | Kelleher | |
| 5,814,029 A | 9/1998 | Hassett | |
| 5,820,591 A | 10/1998 | Thompson et al. | |
| 5,820,592 A | 10/1998 | Hammerslag | |
| 5,820,630 A | 10/1998 | Lind | |
| 5,820,631 A | 10/1998 | Nobles | |
| 5,823,955 A | 10/1998 | Kuck et al. | |
| 5,823,956 A | 10/1998 | Roth et al. | |
| 5,824,065 A | 10/1998 | Gross | |
| 5,827,237 A | 10/1998 | Macoviak et al. | |
| 5,829,447 A | 11/1998 | Stevens et al. | |
| 5,833,671 A | 11/1998 | Macoviak et al. | |
| 5,836,955 A | 11/1998 | Buelna et al. | |
| 5,840,081 A | 11/1998 | Andersen et al. | |
| 5,843,031 A | 12/1998 | Hermann et al. | |
| 5,843,103 A | 12/1998 | Wulfman | |
| 5,849,019 A | 12/1998 | Yoon | |
| 5,853,422 A | 12/1998 | Huebsch et al. | |
| 5,855,271 A | 1/1999 | Eubanks et al. | |
| 5,855,590 A | 1/1999 | Malecki et al. | |
| 5,855,614 A | 1/1999 | Stevens et al. | |
| 5,860,990 A | 1/1999 | Nobles et al. | |
| 5,861,003 A | 1/1999 | Latson et al. | |
| 5,868,733 A | 2/1999 | Ockuly et al. | |
| 5,876,399 A | 3/1999 | Chia et al. | |
| 5,879,307 A | 3/1999 | Chio et al. | |
| 5,885,271 A | 3/1999 | Hamilton et al. | |
| 5,891,160 A | 4/1999 | Williamson et al. | |
| 5,895,404 A | 4/1999 | Ruiz | |
| 5,895,417 A | 4/1999 | Pomeranz et al. | |
| 5,906,620 A * | 5/1999 | Nakao | A61B 17/12013 |
| | | | 606/113 |
| 5,908,420 A | 6/1999 | Parins et al. | |
| 5,916,147 A | 6/1999 | Boury | |
| 5,928,224 A | 7/1999 | Laufer | |
| 5,944,733 A | 8/1999 | Engelson | |
| 5,947,363 A | 9/1999 | Bolduc et al. | |
| 5,954,732 A | 9/1999 | Hart et al. | |
| 5,957,949 A | 9/1999 | Leonhardt et al. | |
| 5,957,973 A | 9/1999 | Quiachon et al. | |
| 5,972,020 A | 10/1999 | Carpentier et al. | |
| 5,972,030 A | 10/1999 | Garrison et al. | |
| 5,980,455 A | 11/1999 | Daniel et al. | |
| 5,989,284 A | 11/1999 | Laufer | |
| 5,997,547 A * | 12/1999 | Nakao | A61B 17/24 |
| | | | 606/113 |
| 6,007,546 A * | 12/1999 | Snow | A61B 18/14 |
| | | | 606/113 |
| 6,015,417 A | 1/2000 | Reynolds, Jr. | |
| 6,019,722 A | 2/2000 | Spence et al. | |
| 6,022,360 A | 2/2000 | Reimels et al. | |
| 6,033,378 A | 3/2000 | Lundquist et al. | |
| 6,036,699 A | 3/2000 | Andreas et al. | |
| 6,048,351 A | 4/2000 | Gordon et al. | |
| 6,056,769 A | 5/2000 | Epstein et al. | |
| 6,059,757 A | 5/2000 | Macoviak et al. | |
| 6,060,628 A | 5/2000 | Aoyama et al. | |
| 6,060,629 A | 5/2000 | Pham et al. | |
| 6,063,106 A | 5/2000 | Gibson | |
| 6,066,146 A | 5/2000 | Carroll et al. | |
| 6,068,628 A | 5/2000 | Fanton et al. | |
| 6,068,629 A | 5/2000 | Haissaguerre et al. | |
| 6,077,214 A | 6/2000 | Mortier et al. | |
| 6,086,600 A | 7/2000 | Kortenbach | |
| 6,088,889 A | 7/2000 | Luther et al. | |
| 6,090,118 A | 7/2000 | McGuckin, Jr. | |
| 6,099,505 A | 8/2000 | Ryan et al. | |
| 6,099,553 A | 8/2000 | Hart et al. | |
| 6,110,145 A | 8/2000 | Macoviak | |
| 6,117,144 A | 9/2000 | Nobles et al. | |
| 6,117,159 A | 9/2000 | Huebsch et al. | |
| 6,123,665 A * | 9/2000 | Kawano | A61B 17/3478 |
| | | | 606/113 |
| 6,123,699 A | 9/2000 | Webster, Jr. | |
| 6,126,658 A | 10/2000 | Baker | |
| 6,132,447 A | 10/2000 | Dorsey | |
| 6,136,010 A | 10/2000 | Modesitt et al. | |
| 6,139,508 A | 10/2000 | Simpson et al. | |
| 6,143,024 A | 11/2000 | Campbell et al. | |
| 6,159,240 A | 12/2000 | Sparer et al. | |
| 6,162,233 A | 12/2000 | Williamson et al. | |
| 6,165,164 A | 12/2000 | Hill et al. | |
| 6,165,183 A | 12/2000 | Kuehn et al. | |
| 6,165,204 A | 12/2000 | Levinson et al. | |
| 6,168,614 B1 | 1/2001 | Andersen et al. | |
| 6,171,320 B1 | 1/2001 | Monassevitch | |
| 6,174,322 B1 | 1/2001 | Schneidt | |
| 6,180,059 B1 | 1/2001 | Divino et al. | |
| 6,182,664 B1 | 2/2001 | Cosgrove | |
| 6,187,003 B1 | 2/2001 | Buysse et al. | |
| 6,190,408 B1 | 2/2001 | Melvin | |
| 6,197,043 B1 | 3/2001 | Davidson | |
| 6,203,531 B1 | 3/2001 | Ockuly et al. | |
| 6,203,553 B1 | 3/2001 | Robertson et al. | |
| 6,206,893 B1 | 3/2001 | Klein et al. | |
| 6,206,907 B1 | 3/2001 | Marino et al. | |
| 6,210,419 B1 | 4/2001 | Mayenberger et al. | |
| 6,210,432 B1 | 4/2001 | Solem et al. | |

(56) References Cited

U.S. PATENT DOCUMENTS

| | | |
|---|---|---|
| 6,245,079 B1 | 6/2001 | Nobles et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,334,860 B1 | 1/2002 | Dorn |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,640 B1 | 7/2002 | Taylor |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,508,828 B1 | 1/2003 | Akerfeldt et al. |
| 6,517,550 B1 | 2/2003 | Konya et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Horner |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,932,810 B2 | 8/2005 | Ryan |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen et al. |
| 7,011,669 B2 | 3/2006 | Kimblad |
| 7,033,390 B2 | 4/2006 | Johnson et al. |
| 7,048,754 B2 | 5/2006 | Martin et al. |
| 7,112,207 B2 | 9/2006 | Allen et al. |
| 7,226,467 B2 | 6/2007 | Lucatero et al. |
| 7,288,097 B2 | 10/2007 | Seguin |
| 7,291,168 B2 | 11/2007 | Macoviak et al. |
| 7,338,467 B2 | 3/2008 | Lutter |
| 7,381,210 B2 | 6/2008 | Zarbatany et al. |
| 7,435,257 B2 | 10/2008 | Lashinski et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,666,204 B2 | 2/2010 | Thornton et al. |
| 7,955,340 B2 | 6/2011 | Michlitsch et al. |
| 8,216,234 B2 | 7/2012 | Long |
| 8,257,356 B2 | 9/2012 | Bleich et al. |
| 8,398,708 B2 | 3/2013 | Meiri et al. |
| 8,435,237 B2 | 5/2013 | Bahney |
| 8,500,768 B2 | 8/2013 | Cohen |
| 8,523,881 B2 | 9/2013 | Cabiri et al. |
| 8,623,077 B2 | 1/2014 | Cohn |
| 8,690,858 B2 | 4/2014 | Machold et al. |
| 8,821,518 B2 | 9/2014 | Saliman et al. |
| 8,926,588 B2 | 1/2015 | Berthiaume et al. |
| 9,126,032 B2 | 9/2015 | Khairkhahan et al. |
| 9,211,119 B2 | 12/2015 | Hendricksen et al. |
| 9,370,341 B2 * | 6/2016 | Ceniccola ........ A61B 17/00234 |
| 9,498,331 B2 | 11/2016 | Chang et al. |
| 9,572,666 B2 | 2/2017 | Basude et al. |
| 9,770,256 B2 | 9/2017 | Cohen et al. |
| 9,949,833 B2 | 4/2018 | McCleary et al. |
| 10,667,804 B2 | 6/2020 | Basude et al. |
| 11,013,554 B2 | 5/2021 | Coates |
| 11,406,250 B2 | 8/2022 | Saadat et al. |
| 2001/0002445 A1 | 5/2001 | Vesely |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2001/0044635 A1 | 11/2001 | Niizeki et al. |
| 2002/0013547 A1 | 1/2002 | Paskar |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hlavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0173811 A1 | 11/2002 | Tu et al. |
| 2002/0173841 A1 | 11/2002 | Ortiz et al. |

(56) References Cited

U.S. PATENT DOCUMENTS

| | | |
|---|---|---|
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Online et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St et al. |
| 2004/0015232 A1 | 1/2004 | Shu et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St et al. |
| 2004/0039442 A1 | 2/2004 | St et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0059345 A1* | 3/2004 | Nakao .................. A61B 18/14 606/113 |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092858 A1 | 5/2004 | Wilson et al. |
| 2004/0092962 A1 | 5/2004 | Thornton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0116848 A1 | 6/2004 | Gardeski et al. |
| 2004/0116951 A1 | 6/2004 | Rosengart |
| 2004/0122448 A1 | 6/2004 | Levine |
| 2004/0127849 A1 | 7/2004 | Kantor |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133232 A1 | 7/2004 | Rosenbluth et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0147826 A1 | 7/2004 | Peterson |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Liska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225233 A1 | 11/2004 | Frankowski et al. |
| 2004/0225300 A1 | 11/2004 | Goldfarb et al. |
| 2004/0225305 A1 | 11/2004 | Ewers et al. |
| 2004/0236354 A1 | 11/2004 | Seguin |
| 2004/0242960 A1* | 12/2004 | Orban, III ............... A61B 10/06 600/106 |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Rahdert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St et al. |
| 2005/0021057 A1 | 1/2005 | St et al. |
| 2005/0021058 A1 | 1/2005 | Negro |
| 2005/0033446 A1 | 2/2005 | Deem et al. |
| 2005/0038383 A1 | 2/2005 | Kelley et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0065453 A1 | 3/2005 | Shabaz et al. |
| 2005/0085903 A1 | 4/2005 | Lau |
| 2005/0119735 A1 | 6/2005 | Spence et al. |
| 2005/0143809 A1 | 6/2005 | Salahieh et al. |
| 2005/0149014 A1 | 7/2005 | Hauck et al. |
| 2005/0159763 A1 | 7/2005 | Mollenauer et al. |
| 2005/0159810 A1 | 7/2005 | Filsoufi |
| 2005/0192633 A1 | 9/2005 | Montpetit |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0256452 A1 | 11/2005 | Demarchi et al. |
| 2005/0267493 A1 | 12/2005 | Schreck et al. |
| 2005/0273160 A1 | 12/2005 | Lashinski et al. |
| 2005/0277876 A1 | 12/2005 | Hayden |
| 2005/0287493 A1 | 12/2005 | Novak et al. |
| 2006/0004247 A1 | 1/2006 | Kute et al. |
| 2006/0009759 A1 | 1/2006 | Chrisitian et al. |
| 2006/0015003 A1 | 1/2006 | Moaddes et al. |
| 2006/0015179 A1 | 1/2006 | Bulman-Fleming et al. |
| 2006/0020275 A1 | 1/2006 | Goldfarb et al. |
| 2006/0020327 A1 | 1/2006 | Lashinski et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0074484 A1 | 4/2006 | Huber |
| 2006/0089671 A1 | 4/2006 | Goldfarb et al. |
| 2006/0089711 A1 | 4/2006 | Dolan |
| 2006/0135961 A1 | 6/2006 | Rosenman et al. |
| 2006/0135993 A1 | 6/2006 | Seguin |
| 2006/0184198 A1 | 8/2006 | Bales et al. |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Rahdert et al. |
| 2006/0276890 A1 | 12/2006 | Solem et al. |
| 2007/0016225 A1 | 1/2007 | Nakao |
| 2007/0038293 A1 | 2/2007 | St et al. |
| 2007/0060997 A1 | 3/2007 | De Boer |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0173757 A1 | 7/2007 | Levine et al. |

(56) References Cited

U.S. PATENT DOCUMENTS

| | | |
|---|---|---|
| 2007/0197858 A1 | 8/2007 | Goldfarb et al. |
| 2007/0198082 A1 | 8/2007 | Kapadia et al. |
| 2007/0260225 A1 | 11/2007 | Sakakine et al. |
| 2007/0287884 A1* | 12/2007 | Schena .................. A61B 34/72 600/104 |
| 2008/0009858 A1 | 1/2008 | Rizvi |
| 2008/0039935 A1 | 2/2008 | Buch et al. |
| 2008/0045936 A1 | 2/2008 | Vaska et al. |
| 2008/0051703 A1 | 2/2008 | Thornton et al. |
| 2008/0051807 A1 | 2/2008 | St et al. |
| 2008/0097467 A1 | 4/2008 | Gruber et al. |
| 2008/0097489 A1 | 4/2008 | Goldfarb et al. |
| 2008/0167714 A1 | 7/2008 | St et al. |
| 2008/0183194 A1 | 7/2008 | Goldfarb et al. |
| 2008/0188850 A1 | 8/2008 | Mody et al. |
| 2008/0195126 A1 | 8/2008 | Solem |
| 2008/0243249 A1 | 10/2008 | Kohm et al. |
| 2008/0294175 A1 | 11/2008 | Bardsley et al. |
| 2008/0312496 A1* | 12/2008 | Zwolinski ........ A61B 17/00234 600/153 |
| 2009/0012538 A1 | 1/2009 | Saliman et al. |
| 2009/0036768 A1 | 2/2009 | Seehusen et al. |
| 2009/0156995 A1 | 6/2009 | Martin et al. |
| 2009/0163934 A1 | 6/2009 | Raschdorf et al. |
| 2009/0177266 A1 | 7/2009 | Powell et al. |
| 2009/0192510 A1* | 7/2009 | Bahney .............. A61B 18/1482 606/45 |
| 2009/0198322 A1 | 8/2009 | Deem et al. |
| 2009/0204005 A1 | 8/2009 | Keast et al. |
| 2009/0209955 A1 | 8/2009 | Forster et al. |
| 2009/0209991 A1 | 8/2009 | Hinchliffe et al. |
| 2009/0270858 A1 | 10/2009 | Hauck et al. |
| 2009/0276039 A1 | 11/2009 | Meretei |
| 2009/0281619 A1 | 11/2009 | Le et al. |
| 2009/0326567 A1 | 12/2009 | Goldfarb et al. |
| 2010/0016958 A1 | 1/2010 | St et al. |
| 2010/0022823 A1 | 1/2010 | Goldfarb et al. |
| 2010/0044410 A1 | 2/2010 | Argentine et al. |
| 2010/0121437 A1 | 5/2010 | Subramanian et al. |
| 2010/0152612 A1* | 6/2010 | Headley, Jr ............ A61B 1/273 600/566 |
| 2010/0217261 A1 | 8/2010 | Watson |
| 2010/0262231 A1 | 10/2010 | Tuval et al. |
| 2010/0268226 A1 | 10/2010 | Epp et al. |
| 2010/0298929 A1 | 11/2010 | Thornton et al. |
| 2011/0009864 A1 | 1/2011 | Bucciaglia et al. |
| 2011/0184405 A1 | 7/2011 | Mueller |
| 2011/0224710 A1 | 9/2011 | Bleich |
| 2011/0238052 A1 | 9/2011 | Robinson |
| 2012/0022527 A1 | 1/2012 | Woodruff et al. |
| 2012/0022640 A1 | 1/2012 | Gross et al. |
| 2012/0065464 A1 | 3/2012 | Ellis et al. |
| 2012/0150194 A1 | 6/2012 | Odermatt et al. |
| 2012/0172915 A1 | 7/2012 | Fifer et al. |
| 2012/0179184 A1 | 7/2012 | Orlov |
| 2012/0265222 A1 | 10/2012 | Gordin et al. |
| 2012/0310330 A1 | 12/2012 | Buchbinder et al. |
| 2012/0316639 A1 | 12/2012 | Kleinschrodt |
| 2012/0330348 A1 | 12/2012 | Strauss et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0109910 A1 | 5/2013 | Alexander et al. |
| 2013/0172828 A1* | 7/2013 | Kappel ............ A61B 17/32056 606/174 |
| 2013/0317515 A1 | 11/2013 | Kuroda et al. |
| 2014/0039511 A1 | 2/2014 | Morris et al. |
| 2014/0135799 A1 | 5/2014 | Henderson |
| 2014/0228871 A1 | 8/2014 | Cohen et al. |
| 2014/0276913 A1 | 9/2014 | Tah et al. |
| 2014/0309670 A1 | 10/2014 | Bakos et al. |
| 2014/0324164 A1 | 10/2014 | Gross et al. |
| 2014/0350662 A1 | 11/2014 | Mordehay |
| 2014/0358224 A1 | 12/2014 | Tegels et al. |
| 2014/0364866 A1* | 12/2014 | Dryden ............ A61B 17/32056 606/113 |
| 2014/0379074 A1 | 12/2014 | Spence et al. |
| 2015/0005704 A1 | 1/2015 | Heisel et al. |
| 2015/0005801 A1 | 1/2015 | Marquis et al. |
| 2015/0051698 A1 | 2/2015 | Ruyra et al. |
| 2015/0094800 A1 | 4/2015 | Chawla |
| 2015/0112430 A1 | 4/2015 | Creaven et al. |
| 2015/0211946 A1 | 7/2015 | Pons et al. |
| 2015/0230947 A1 | 8/2015 | Krieger et al. |
| 2015/0257877 A1 | 9/2015 | Hernandez |
| 2015/0257883 A1 | 9/2015 | Basude et al. |
| 2015/0306806 A1 | 10/2015 | Dando et al. |
| 2016/0015410 A1 | 1/2016 | Asirvatham et al. |
| 2016/0074165 A1 | 3/2016 | Spence et al. |
| 2016/0174979 A1 | 6/2016 | Wei |
| 2017/0042678 A1 | 2/2017 | Ganesan et al. |
| 2017/0100183 A1* | 4/2017 | Iaizzo ................ A61B 18/1492 |
| 2017/0143330 A1 | 5/2017 | Basude et al. |
| 2017/0202559 A1 | 7/2017 | Taha |
| 2017/0232238 A1 | 8/2017 | Biller et al. |
| 2018/0008268 A1 | 1/2018 | Khairkhahan |
| 2018/0028215 A1 | 2/2018 | Cohen |
| 2018/0092661 A1 | 4/2018 | Prabhu |
| 2018/0133010 A1 | 5/2018 | Kizuka |
| 2018/0161159 A1 | 6/2018 | Lee et al. |
| 2018/0360457 A1 | 12/2018 | Ellis et al. |
| 2019/0029790 A1 | 1/2019 | Bak-Boychuk et al. |
| 2019/0183571 A1 | 6/2019 | De Marchena |
| 2019/0298517 A1 | 10/2019 | Sanchez et al. |
| 2020/0121460 A1 | 4/2020 | Dale et al. |

FOREIGN PATENT DOCUMENTS

| | | |
|---|---|---|
| CN | 103841899 A | 6/2014 |
| CN | 104244841 A | 12/2014 |
| DE | 3504292 C1 | 7/1986 |
| DE | 9100873 U1 | 4/1991 |
| DE | 10116168 A1 | 11/2001 |
| EP | 0179562 A1 | 4/1986 |
| EP | 0558031 A2 | 9/1993 |
| EP | 0684012 A2 | 11/1995 |
| EP | 0727239 A2 | 8/1996 |
| EP | 0782836 A1 | 7/1997 |
| EP | 1230899 A1 | 8/2002 |
| EP | 1674040 A2 | 6/2006 |
| EP | 1980288 A1 | 10/2008 |
| EP | 2005912 A2 | 12/2008 |
| EP | 2537487 A1 | 12/2012 |
| EP | 2641570 A1 | 9/2013 |
| EP | 2702965 A1 | 3/2014 |
| EP | 3009103 A1 | 4/2016 |
| FR | 2705556 A1 | 12/1994 |
| FR | 2768324 A1 | 3/1999 |
| FR | 2903292 A1 | 1/2008 |
| GB | 1598111 A | 9/1981 |
| GB | 2151142 A | 7/1985 |
| JP | 09-253030 A | 9/1997 |
| JP | 11-089937 A | 4/1999 |
| JP | 2000-283130 A | 10/2000 |
| JP | 2006-528911 A | 12/2006 |
| JP | 2013-516244 A | 5/2013 |
| JP | 2014-523274 A | 9/2014 |
| JP | 2015-502548 A | 1/2015 |
| WO | 81/00668 A1 | 3/1981 |
| WO | 91/01689 A1 | 2/1991 |
| WO | 91/18881 A1 | 12/1991 |
| WO | 92/12690 A1 | 8/1992 |
| WO | 94/18881 A1 | 9/1994 |
| WO | 94/18893 A1 | 9/1994 |
| WO | 95/08292 A1 | 3/1995 |
| WO | 95/11620 A2 | 5/1995 |
| WO | 95/15715 A1 | 6/1995 |
| WO | 96/14032 A1 | 5/1996 |
| WO | 96/20655 A1 | 7/1996 |
| WO | 96/22735 A1 | 8/1996 |
| WO | 96/30072 A1 | 10/1996 |
| WO | 97/18746 A2 | 5/1997 |
| WO | 97/25927 A1 | 7/1997 |

(56) References Cited

FOREIGN PATENT DOCUMENTS

| | | |
|---|---|---|
| WO | 97/26034 A1 | 7/1997 |
| WO | 97/38748 A2 | 10/1997 |
| WO | 97/39688 A2 | 10/1997 |
| WO | 97/48436 A2 | 12/1997 |
| WO | 98/07375 A1 | 2/1998 |
| WO | 98/24372 A1 | 6/1998 |
| WO | 98/30153 A1 | 7/1998 |
| WO | 98/32382 A1 | 7/1998 |
| WO | 98/35638 A1 | 8/1998 |
| WO | 99/00059 A1 | 1/1999 |
| WO | 99/01377 A1 | 1/1999 |
| WO | 99/07295 A1 | 2/1999 |
| WO | 99/07354 A2 | 2/1999 |
| WO | 99/13777 A1 | 3/1999 |
| WO | 99/44524 A2 | 9/1999 |
| WO | 99/66967 A1 | 12/1999 |
| WO | 00/02489 A1 | 1/2000 |
| WO | 00/03651 A1 | 1/2000 |
| WO | 00/03759 A2 | 1/2000 |
| WO | 00/12168 A1 | 3/2000 |
| WO | 00/44313 A1 | 8/2000 |
| WO | 00/59382 A1 | 10/2000 |
| WO | 00/60995 A2 | 10/2000 |
| WO | 01/00111 A1 | 1/2001 |
| WO | 01/00114 A1 | 1/2001 |
| WO | 01/03651 A2 | 1/2001 |
| WO | 01/26557 A1 | 4/2001 |
| WO | 01/26586 A1 | 4/2001 |
| WO | 01/26587 A1 | 4/2001 |
| WO | 01/26588 A2 | 4/2001 |
| WO | 01/26703 A1 | 4/2001 |
| WO | 01/28432 A1 | 4/2001 |
| WO | 01/28455 A1 | 4/2001 |
| WO | 01/47438 A1 | 7/2001 |
| WO | 01/49213 A2 | 7/2001 |
| WO | 01/50985 A1 | 7/2001 |
| WO | 01/54618 A1 | 8/2001 |
| WO | 01/56512 A1 | 8/2001 |
| WO | 01/66001 A2 | 9/2001 |
| WO | 01/70320 A1 | 9/2001 |
| WO | 01/89440 A2 | 11/2001 |
| WO | 01/95831 A2 | 12/2001 |
| WO | 01/95832 A2 | 12/2001 |
| WO | 01/97741 A2 | 12/2001 |
| WO | 02/00099 A2 | 1/2002 |
| WO | 02/01999 A2 | 1/2002 |
| WO | 02/03892 A1 | 1/2002 |
| WO | 02/34167 A2 | 5/2002 |
| WO | 02/60352 | 8/2002 |
| WO | 02/62263 | 8/2002 |
| WO | 02/62270 | 8/2002 |
| WO | 02/62408 | 8/2002 |
| WO | 03/01893 A2 | 1/2003 |
| WO | 03/03930 | 1/2003 |
| WO | 03/20179 | 3/2003 |
| WO | 03/28558 A2 | 4/2003 |
| WO | 03/37171 | 5/2003 |
| WO | 03/47467 | 6/2003 |
| WO | 03/49619 | 6/2003 |
| WO | 03/73910 | 9/2003 |
| WO | 03/73913 | 9/2003 |
| WO | 03/82129 | 10/2003 |
| WO | 2003/105667 | 12/2003 |
| WO | 2004/004607 A1 | 1/2004 |
| WO | 2004/006810 A1 | 1/2004 |
| WO | 2004/012583 A2 | 2/2004 |
| WO | 2004/012789 A2 | 2/2004 |
| WO | 2004/014282 A2 | 2/2004 |
| WO | 2004/019811 A2 | 3/2004 |
| WO | 2004/030570 A2 | 4/2004 |
| WO | 2004/037317 A2 | 5/2004 |
| WO | 2004/045370 A2 | 6/2004 |
| WO | 2004/045378 A2 | 6/2004 |
| WO | 2004/045463 A2 | 6/2004 |
| WO | 2004/047679 A1 | 6/2004 |
| WO | 2004/062725 A1 | 7/2004 |
| WO | 2004/082523 A2 | 9/2004 |
| WO | 2004/082538 A2 | 9/2004 |
| WO | 2004/093730 A2 | 11/2004 |
| WO | 2004/103162 A2 | 12/2004 |
| WO | 2004/112585 A2 | 12/2004 |
| WO | 2004/112651 A2 | 12/2004 |
| WO | 2005/002424 A2 | 1/2005 |
| WO | 2005/018507 A2 | 3/2005 |
| WO | 2005/027797 A1 | 3/2005 |
| WO | 2005/032421 A2 | 4/2005 |
| WO | 2005/062931 A2 | 7/2005 |
| WO | 2005/112792 A2 | 12/2005 |
| WO | 2006/037073 A2 | 4/2006 |
| WO | 2006/105008 A1 | 10/2006 |
| WO | 2006/105009 A1 | 10/2006 |
| WO | 2006/113906 A1 | 10/2006 |
| WO | 2006/115875 A2 | 11/2006 |
| WO | 2006/115876 A2 | 11/2006 |
| WO | 2007/136829 A1 | 11/2007 |
| WO | 2008/103722 A2 | 8/2008 |
| WO | 2010/024801 A1 | 3/2010 |
| WO | 2010/121076 A2 | 10/2010 |
| WO | 2012/020521 A1 | 2/2012 |
| WO | 2013/049734 A1 | 4/2013 |
| WO | 2013/103934 A1 | 7/2013 |
| WO | 2014/064694 A2 | 5/2014 |
| WO | 2014/121280 A2 | 8/2014 |
| WO | 2016/022797 A1 | 2/2016 |
| WO | 2016/144708 A1 | 9/2016 |
| WO | 2016/150806 A1 | 9/2016 |
| WO | 2017/223073 A1 | 12/2017 |
| WO | 2018/009718 A1 | 1/2018 |
| WO | 2018/106482 A2 | 6/2018 |
| WO | 2018/236766 A1 | 12/2018 |
| WO | 2019/040943 A1 | 2/2019 |
| WO | 2019/195336 A1 | 10/2019 |

OTHER PUBLICATIONS

Office Action received for U.S. Appl. No. 15/642,245, dated Aug. 9, 2019.

Office Action received for U.S. Appl. No. 15/724,545, filed Dec. 27, 2019.

Office Action received for U.S. Appl. No. 15/724,545, dated Dec. 27, 2019.

Office Action received for U.S. Appl. No. 15/724,545, dated May 1, 2020.

Osawa et al., "Partial Left Ventriculectomy in a 3-Year Old Boy with Dilated Cardiomyopathy," Japanese Journal of Thoracic and Cardiovascular Surg, 48:590-593 (2000).

Park et al., Clinical Use of Blade Atrial Septostomy, Circulation, 1978, pp. 600-608, vol. 58.

Park et al., Clinical Use of Blade Atrial Septostomy, Circulation, pp. 600-608, vol. 58, No. 4 (1978).

Patel et al., #57 Epicardial Atrial Defibrillation: Novel Treatment of Postoperative Atrial Fibrillation, 2003 STS Presentation, [Abstract Only].

Privitera et al., "Alfieri Mitral Valve Repair: Clinical Outcome and Pathology," Circulation, 106:e173-e174 (2002).

Redaelli et al., "A Computational Study of the Hemodynamics After 'Edge-To-Edge' Mitral Valve Repair," Journal of Biomechanical Engineering, 123:565-570 (2001).

Reul et al., "Mitral Valve Reconstruction for Mitral Insufficiency," Progress in Cardiovascular Diseases, XXXIX(6):567-599 (1997).

Ricchi et al, Linear Segmental Annuloplasty for Mitral Valve Repair, Ann. Thorac. Surg., Jan. 7, 1997, pp. 1805-1806, vol. 63.

Ricchi et al., Linear Segmental Annuloplasty for Milral Valve Repair, Ann. Thorac. Surg., Jan. 7, 1997, pp. 1805-1806, vol. 63.

Robicsek et al., #60 The Bicuspid Aortic Valve: How Does It Function? Why Does It Fail? 2003 STS Presentation, [Abstract Only].

Rose et al., "Late MitraClip Failure: Removal Technique for Leaflet-Sparing Mitral Valve Repair", Journal of Cardiac Surgery, (Jul. 4, 2012), XP055047339, DOI: 10.1111/j. 1540- 8191.2012.01483.x [retrieved on Dec. 11, 2012].

(56) References Cited

OTHER PUBLICATIONS

Supplemental European Search Report of EP Application No. 02746781, dated May 13, 2008, 3 pages total.
Supplementary European Search Report issued in European Application No. 05753261.6 dated Jun. 9, 2011, 3 pages total.
Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.
Tager et al., Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiel., Apr. 15, 1998, pp. 1013-1016, vol. 81.
Takizawa H et al: Development of a microfine active bending catheter equipped with MIF tactile sensors", Micro Electro Mechanical Systems, 1999. MEMS '99. Twelfth IEEE Interna Tional Conference on Orlando, FL, USA Jan. 17-21, 1999, Piscataway, NJ, USA,IEEE, US, Jan. 17, 1999 (Jan. 17, 1999), pp. 412-417, XP010321677, ISBN: 978-0-7803-5194-3 figures 1-3."
Tamura et al., "Edge to Edge Repair for Mitral Regurgitation in a Patient with Chronic Hemodialysis: Report of a Case," Kyobu Geka. The Japanese Journal of Thoracic Surgery, 54(9):788-790 (2001).
Tibayan et al., #59 Annular Geometric Remodeling in Chronic Ischemic Mitral Regurgitation, 2003 STS Presentation, [Abstract Only].
Timek et al., "Edge-to-edge mitral repair: gradients and three-dimensional annular dynamics in vivo during inotropic stimulation," Eur J. of Cardiothoracic Surg., 19:431-437 (2001).
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
Totaro, "Mitral valve repair for isolated prolapse of the anterior leaflet: an 11-year follow-up," European Journal of Cardio-thoracic Surgery, 15:119-126 (1999).
U.S. Provisional Application filed Jul. 6, 2016, by Khairkhahan., U.S. Appl. No. 62/359,121.
U.S. Provisional Application filed Nov. 7, 2016, by Khairkhahan., U.S. Appl. No. 62/418,571.
U.S. Provisional Application filed Oct. 22, 2018, by Dale et al., U.S. Appl. No. 62/748,947.
Uchida et al, Percutaneous Cardiomyotomy and Valvulotomy with Angioscopic Guidance, Am. Heart J., Apr. 1991, pp. 1221-1224, vol. 121.
Uchida et al., Percutaneous Cardiomyotomy and Valvulotomy with Angioscopic Guidance, Am. Heart J., pp. 1221-1224, vol. 121 (Apr. 1991).
Umana et al, 'Bow-Tie' Mitral Valve Repair: An Adjuvant Technique for Ischemic Mitral Regurgitation, Ann. Thorac. Surg., May 12, 1998, pp. 1640-1646, vol. 66.
Umana et al., "'Bow-tie' Mitral Valve Repair Successfully Addresses Subvalvular Dysfunction in Ischemic Mitral Regurgitation," Surgical Forum, XLVI11:279-280 (1997).
U.S. Appl. No. 14/216,813, filed Mar. 17, 2014, Hernandez.
Votta et al., "3-D Computational Analysis of the Stress Distribution on the Leaflets after Edge-to-Edge Repair of Mitral Regurgitation," Journal of Heart Valve Disease, 11:810-822 (2002).
Abe et al, "De Vega's Annuloplasty for Acquired Tricuspid Disease: Early and Late Results in 110 Patients", Ann. Thorac. Surg., pp. 670-676, vol. 48 (Jan. 1989).
Abe et al., "Updated in 1996—De Vega's Annuloplasty for Acquired Tricuspid Disease: Early and Late Results in 110 Patients", Ann. Thorac. Surg., pp. 1876-1877, vol. 62 (1996).
Agricola et al., "Mitral Valve Reserve in Double Orifice Technique: an Exercise Echocardiographic Study," Journal of Heart Valve Disease, 11(5):637-643 (2002).
Alfieri et al., "An Effective Technique to Correct Anterior Mitral Leaflet Prolapse," J. Card Surg., 14:468-470 (1999).
Alfieri et al., "Novel Suture Device for Beating Heart Mitral Leaflet Approximation," Annals of Thoracic Surgery, 74:1488-1493 (2002).
Alfieri et al., "The double orifice technique in mitral valve repair: a simple solution for complex problems," Journal of Thoracic and Cardiovascular Surgery, 122:674-681 (2001).
Alfieri et al., "The Edge to Edge Technique," The European Association For Cardio—Thoracic Surgery, 14th Annual Meeting, Frankfurt/ Germany, Oct. 7-11, 2000, Post Graduate Courses, Book of Proceedings.
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Ali Khan et al, Blade Atrial Septostomy: Experience with the First 50 Procedures, Cathet. Cardiovasc. Diagn., Aug. 1991, pp. 257-262, vol. 23.
Alvarez et al, Repairing the Degenerative Mitral Valve: Ten to Fifteen-year Follow-up, Journal of Thoracic Cardiovascular Surgery, Aug. 1996, pp. 238-247, vol. 112, No. 2.
Alvarez et al, Repairing the Degenerative Mitral Valve: Ten to Fifteen-year Follow-up, Journal Thoracic of Cardiovascular Surgery, Aug. 1996, pp. 238-247, vol. 112, No. 2.
Arisi et al., "Mitral Valve Repair with Alfieri Technique in Mitral Regurgitation of Diverse Etiology: Early Echocardiographic Results," Circulation Supplement II, 104(17):3240 (2001).
Bach et al, Early Improvement in Congestive Heart Failure After Correction of Secondary Mitral Regurgitation in End-stage Cardiomyopathy, American Heart Journal, Jun. 1995, pp. 1165-1170, vol. 129, No. 6.
Bach et al, Improvement Following Correction of Secondary Mitral Regurgitation in End-stage Cardiomyopathy With Mitral Annuloplasty, Am. J. Cardiol., Oct. 15, 1996, pp. 966-969, vol. 78.
Bach et al, Improvement Following Correction of Secondary Mitral Regurgitation in End-stage Cardiomyopathy With Mitral Annuloplasty, Am J_ Cardiel., Oct. 15, 1996, pp. 966-969, vol. 78.
Bailey, "Mitral Regurgitation" in Surgery of the Heart, Chapter 20, pp. 686-737 (1955).
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only], 2004.
Bolling et al, Surgery for Acquired Heart Disease: Early Outcome of Mitral Valve Reconstruction in Patients with End-stage Cardiomyopathy, Journal of Thoracic and Cariovascular Surgery, Apr. 1995, pp. 676-683, vol. 109, No. 4.
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action issued in Chinese Application No. 200980158707.2 dated Sep. 9, 2013.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Communication dated May 8, 2017, from the European Patent Office in counterpart European Application No. 04752714.8.
Dang N C et al., "Surgical Revision After Percutaneous Mitral Valve Repair with a Clip: Initial Multicenter Experience",THE Annals of Thracic SURGERY,Elsevier, United States, vol. 80, No. 6, pp. 2338-2342, (Dec. 1, 2005), XP027732951, ISSN:0003-4975 [retrieved on Dec. 1, 2005].
Dec et al, Idiopathic Dilated Cardiomyopathy, The New England Journal of Medicine, Dec. 8, 1994, pp. 1564-1575, vol. 331, No. 23.
Dottori et al., "Echocardiographic imaging of the Alfieri type mitral valve repair," Itai. Heart J., 2(4):319-320 (2001).

(56) References Cited

OTHER PUBLICATIONS

Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Feldman, et al. Randomized Comparison of Percutaneous Repair and Surgery for Mitral Regurgitation: 5-Year Results of Everest II. J Am Coll Cardiol. Dec. 29, 2015;66(25):2844-2854.
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).
Frazier et al., #62 Early Clinical Experience with an Implantable, Intracardiac Circulatory Support Device: Operative Considerations and Physiologic Implications, 2003 STS Presentation, 1 page total. [Abstract Only].
Fucci et al, Improved Results with Mitral Valve Repair Using New Surgical Techniques, Eur. J. Cardiothorac. Surg., Nov. 1995, pp. 621-627, vol. 9.
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Garcia-Rinaldi et al., "Left Ventricular Volume Reduction and Reconstruction is Ischemic Cardiomyopathy," Journal of Cardiac Surgery, 14:199-210 (1999).
Gateliene, "Early and postoperative results results of metal and tricuspid valve insufficiency surgical treatment using edge-to-edge central coaptation procedure," (Oct. 2002) 38 (Suppl 2):172 175.
Gatti et al., "The edge to edge technique as a trick to rescue an imperfect mitral valve repair," Eur. J. Cardiothorac Surg, 22:817-820 (2002).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
Izzat et al., "Early Experience with Partial Left Ventriculectomy in the Asia-Pacific Region," Annals of Thoracic Surgery, 67:1703-1707 (1999).
Kallner et al., "Transaortic Approach for the Alfieri Stitch," Ann Thorac Surg, 71:378-380 (2001).
Kameda et al, Annuloplasty for Severe Milral Regurgitation Due to Dilated Cardiomyopathy, Ann. Thorac. Surg., 1996, pp. 1829-1832, vol. 61.
Kameda et al, Annuloplasty for Severe Mitral Regurgitation Due to Dilated Cardiomyopathy, Ann. Thorac. Surg., 1996, pp. 1829-1832, vol. 61.
Kavarana et al., "Transaortic Repair of Mitral Regurgitation," The Heart Surgery Forum, #2000-2389, 3(1):24-28 (2000).
Kaza et al., "Ventricular Reconstruction Results in Improved Left Ventricular Function and Amelioration of Mitral Insufficiency," Annals of Surgery, 235(6):828-832 (2002).
Khan et al., "Blade Atrial Septostomy; Experience with the First 50 Procedures", Catheterization and Cardiovascular Diagnosis, 23:257-262 (1991).
Kherani et al., "The Edge-To-Edge Mitral Valve Repair: The Columbia Presbyterian Experience," Ann. Thorac. Surg., 78:73-76 (2004).

Kron et al., "Surgical Relocation of the Posterior Papillary Muscle in Chronic Ischemic Mitral Regurgitation," Annals. of Thoracic Surgery, 74:600-601 (2002).
Kruger et al., "P73-Edge to Edge Technique in Complex Mitral Valve Repair," Thorac Cardiovasc Surg., 48(Suppl. 1):106 (2000).
Langer et al., "Posterier mitral leaflet extensions: An adjunctive repair option for ischemic mitral regurgitation?" J Thorac Cardiovasc Surg, 131:868-877 (2006).
Lorusso et al., "The double-orifice technique for mitral valve reconstruction: predictors of postoperative outcome," Eur J. Cardiothorac Surg, 20:583-589 (2001).
Maisano et al., The Edge-to-edge Technique: A Simplified Method to Correct Mitral Insufficiency, Eur. J. Cardiothorac. Surg , Jan. 14, 1998, pp. 240-246, vol. 13.
Maisano et al., The future of transcatheter mitral valve interventions: competitive or complementary role of repair vs. replacement? Eur Heart J. Jul. 7, 2015; 36(26):1651-1659.
Maisano et al., "The double orifice repair for Barlow Disease: a simple solution for a complex repair," Supplement in Circulation, (Nov. 1999); 100(18):1-94.
Maisano et al.,"The double orifice technique as a standardized approach to treat mitral regurgitation due to severe myxomatous disease: surgical technique," European Journal of Cardio-thoracic Surgery, 17:201-205 (2000).
Maisano et al., "The Future of Transcatheter Mitral Valve Interventions: Competitive or Complementary Role of Repair vs. Replacement?", Eur Heart J.36(26):1651-1659 (Jul. 7, 2015).
Maisano et al.,"The hemodynamic effects of double-orifice valve repair for mitral regurgitation: a 3D computational model," European Journal of Cardio-thoracic Surgery, 15:419-425 (1999).
Maisano et al., "Valve repair for traumatic tricuspid regurgitation," Eur. J. Cardio-thorac Surg, (1996) 10:867-873.
Maisano et al., 'The Edge-to-edge Technique: A Simplified Method to Correct Mitral Insufficiency, Eur. J. Cardiothorac. Surg., pp. 240-246, vol. 13 (Jan. 14, 1998).
Mantovani et al., "Edge-to-edge Repair of Congenital Familiar Tricuspid Regurgitation: Case Report," J. Heart Valve Dis., 9:641-643 (2000).
McCarthy et al, "Tricuspid Valve Repair With the Cosgrove-Edwards Annuloplasty System", Ann. Thorac. Surg., 64:267-8 ( Jan. 16, 1997).
McCarthy et al., "Partial left ventriculectomy and mitral valve repair for end-stage congestive heart failure," European Journal of Cardio-thoracic Surgery, 13:337-343 (1998).
McCarthy et al., "Tricuspid Valve Repair With the Cosgrove-Edwards Annuloplasty System", Ann. Throac Surg. 64:267-8 (Jan. 16, 1997).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. 1):1-29-1-35 (2001).
Nishimura, et al. 2014 AHA/ACC guideline for the management of patients with valvular heart disease: executive summary: a report of the American College of Cardiology/American Heart Association Task Force on Practice Guidelines. J Am Coll Cardiol. Jun. 10, 2014;63(22):2438-88.
Noera et al., "Tricuspid Valve Incompetence Caused by Nonpenetrating Thoracic Trauma", Annals of Thoracic Surgery, 51:320-322 (1991).
Notice of Allowance received for U.S. Appl. No. 14/216,787, filed Nov. 7, 2016.
Notice of Allowance received for U.S. Appl. No. 14/216,787, dated Nov. 7, 2016.
Notice of Allowance received for U.S. Appl. No. 14/577,852, filed Apr. 25, 2018.

(56) References Cited

OTHER PUBLICATIONS

Notice of Allowance received for U.S. Appl. No. 14/577,852, dated Apr. 25, 2018.
Notice of Allowance received for U.S. Appl. No. 15/642,245, dated Jan. 29, 2020.
Notice of Allowance received for U.S. Appl. No. 15/642,245, dated Mar. 27, 2020.
Notice of Allowance received for U.S. Appl. No. 15/642,245, dated Nov. 6, 2019.
Notice of Allowance received for U.S. Appl. No. 15/423,060, dated Jan. 27, 2020.
Office Action received for U.S. Appl. No. 14/216,787, filed Apr. 8, 2016.
Office Action received for U.S. Appl. No. 14/216,787, dated Apr. 8, 2016.
Office Action received for U.S. Appl. No. 14/216,813, filed Apr. 6, 2018.
Office Action received for U.S. Appl. No. 14/216,813, filed Dec. 15, 2017.
Office Action received for U.S. Appl. No. 14/216,813, filed Mar. 9, 2017.
Office Action received for U.S. Appl. No. 14/216,813, dated Apr. 6, 2018.
Office Action received for U.S. Appl. No. 14/216,813, dated Dec. 15, 2017.
Office Action received for U.S. Appl. No. 14/216,813, dated Mar. 9, 2017.
Office Action received for U.S. Appl. No. 14/577,852, filed May 16, 2017.
Office Action received for U.S. Appl. No. 14/577,852, filed Oct. 20, 2016.
Office Action received for U.S. Appl. No. 14/577,852, filed Sep. 7, 2017.
Office Action received for U.S. Appl. No. 14/577,852, dated May 16, 2017.
Office Action received for U.S. Appl. No. 14/577,852, dated Oct. 20, 2016.
Office Action received for U.S. Appl. No. 14/577,852, dated Sep. 7, 2017.
Office Action received for U.S. Appl. No. 15/423,060, dated Apr. 25, 2019.
Office Action received for U.S. Appl. No. 15/423,060, dated Aug. 19, 2019.

* cited by examiner

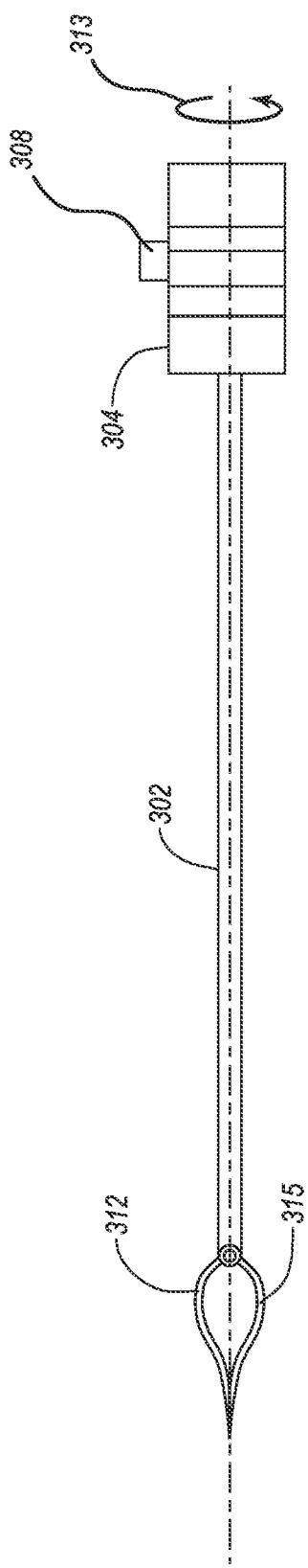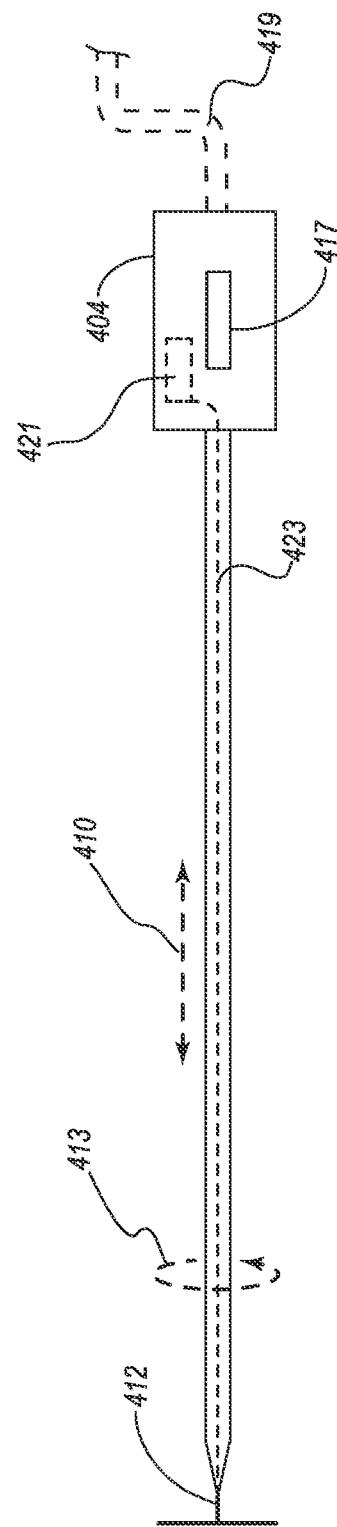

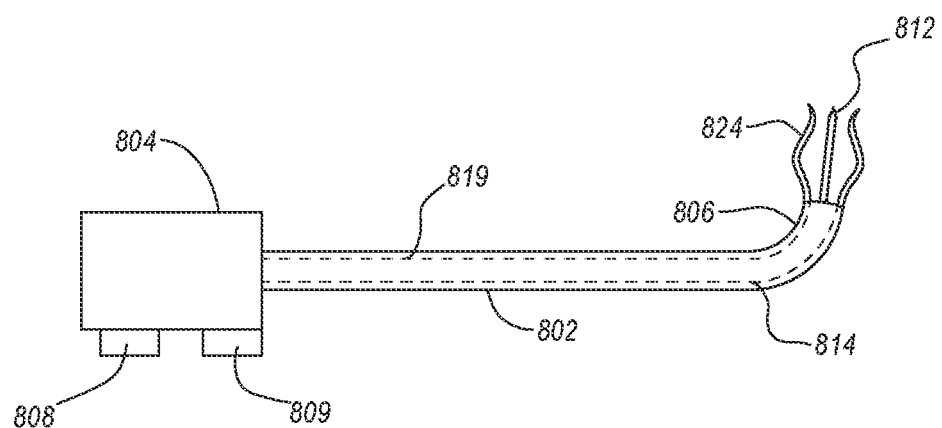
FIG. 9
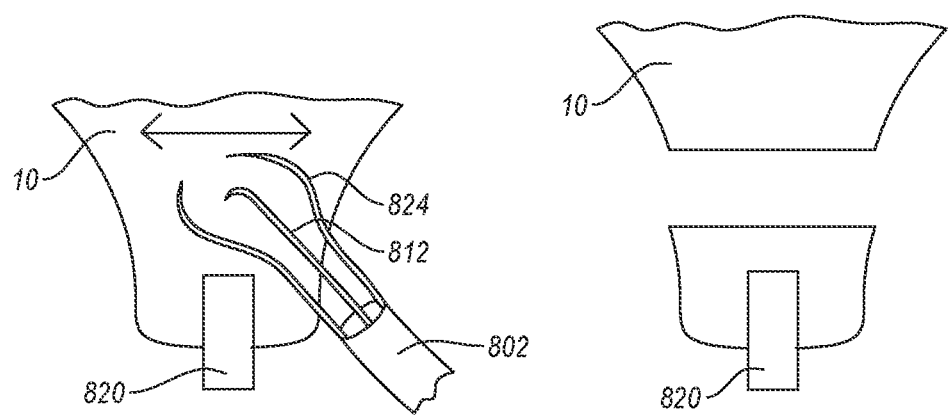
FIG. 10A
FIG. 10B

CARDIAC VALVE CUTTING DEVICE

CROSS-REFERENCE TO RELATED APPLICATIONS

This application is a divisional of U.S. patent application Ser. No. 15/724,545, filed Oct. 4, 2017, titled "Cardiac Valve Cutting Device," which claims the benefit of and priority to U.S. Provisional Patent Application Ser. No. 62/404,558, filed Oct. 5, 2016, titled "Cardiac Valve Cutting Device," the disclosure of which is incorporated herein by this reference in its entirety.

BACKGROUND

The mitral valve controls blood flow from the left atrium to the left ventricle of the heart, preventing blood from flowing backwards from the left ventricle into the left atrium so that it is instead forced through the aortic valve for delivery of oxygenated blood throughout the body. A properly functioning mitral valve opens and closes to enable blood flow in one direction. However, in some circumstances the mitral valve is unable to close properly, allowing blood to regurgitate back into the atrium. Such regurgitation can result in shortness of breath, fatigue, heart arrhythmias, and even heart failure.

Mitral valve regurgitation has several causes. Functional mitral valve regurgitation (FMR) is characterized by structurally normal mitral valve leaflets that are nevertheless unable to properly coapt with one another to close properly due to other structural deformations of surrounding heart structures. Other causes of mitral valve regurgitation are related to defects of the mitral valve leaflets, mitral valve annulus, or other mitral valve tissues. In some circumstances, mitral valve regurgitation is a result of infective endocarditis, blunt chest trauma, rheumatic fever, Marfan syndrome, carcinoid syndrome, or congenital defects to the structure of the heart. Other cardiac valves, in particular the tricuspid valve, can similarly fail to properly close, resulting in undesirable regurgitation.

Heart valve regurgitation is often treated by replacing the faulty valve with a replacement valve implant or by repairing the valve through an interventional procedure. In many instances, a procedure for implanting a replacement heart valve is performed on a patient that has undergone a previous repair procedure for treating the targeted valve, and the targeted valve to be replaced is already associated with an interventional implant. For example, a clip device may have been deployed at the targeted heart valve to fix or approximate leaflets of the valve to reduce regurgitation at the valve. In some circumstances, however, further degradation of the treated heart valve or other clinical circumstances can necessitate that the valve be replaced. In such cases, the previously deployed interventional implant must first be unfixed and/or extracted to prepare the site for deployment and positioning of the replacement valve. As a result, challenges can arise related to the handling of the prior implant(s) and preparation of the targeted site.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Certain embodiments described herein are directed to interventional devices for cutting tissue at a targeted cardiac valve, such as a mitral valve. One or more embodiments described herein enable detachment and/or removal of an implanted repair device from the cardiac valve in order to prepare the valve site to subsequently receive a replacement cardiac valve or other implant, or to receive other treatment.

In some embodiments, an interventional device includes a catheter having a proximal end and a distal end. The distal end is positionable at the targeted cardiac valve. A cutting mechanism is positionable at the distal end of the catheter. The cutting mechanism includes one or more cutting elements configured to cut valve tissue when engaged against the valve tissue. In some embodiments, the interventional device also includes a handle coupled to the proximal end of the catheter. The handle includes one or more cutting controls operatively coupled to the cutting mechanism to provide selective actuation of the cutting mechanism.

In some embodiments, the catheter is configured as a steerable catheter having a steerable distal end. The catheter includes one or more control lines extending from one or more steering controls of the handle to the distal end such that adjusting the tension of the one or more control lines causes deflection of the steerable distal end.

In some embodiments, the cutting mechanism is translatable within the catheter such that it is routable through the catheter to be passed beyond the distal end of the catheter and/or to be retracted proximally into the catheter. In some embodiments, the cutting mechanism includes blades arranged in a scissor-like fashion. In some embodiments, the cutting mechanism includes a cutting element configured as a needle structure and/or includes a cutting element configured as a blade structure. In some embodiments, the cutting mechanism is operatively coupled to the one or more cutting controls via one or more cutting control lines and/or an actuator rod.

In some embodiments, the handle includes or is connected to an electrical source for powering oscillating motion of the one or more cutting elements. In some embodiments, the cutting mechanism is configured to pass radio frequency electrical current and/or thermal energy to the targeted valve to cut the targeted valve.

In some embodiments, the cutting mechanism includes a noose structure positionable around valve tissue, the noose structure being configured to be selectively tightened around valve tissue to cut the valve tissue. In certain embodiments, the noose structure is formed from a hooked wire and a snare, the snare being configured to engage with the hooked wire to complete the noose structure, wherein one or both of the hooked wire and the snare are translatable relative to the distal end of the catheter. In other embodiments, the cutting system includes a first wire and a second wire, each extending distally past the distal end of the catheter, and first and second magnets (e.g., permanent magnets or electromagnets) respectively attached to the distal ends of the first and second wires. The magnets may be coupled to one another such that the first and second wires form the noose. In some embodiments including a noose structure, the targeted leaflet tissue may be cut by mechanically tightening the noose. Alternately, the targeted leaflet may be cut by contacting the noose to the tissue and applying radio frequency electrical and/or thermal energy.

In some embodiments, the cutting system includes one or more stabilizing prongs extendable distally past the distal end of the catheter, the one or more stabilizing prongs being configured to engage against tissue at the targeted valve to stabilize the distal end of the catheter relative to the targeted valve. In some embodiments, the cutting system includes a stabilizing cup which is extendable distally past the distal end of the catheter and is configured to engage with targeted leaflet tissue. The cup may also be configured to hold an interventional device implanted into the leaflet tissue such that the interventional device may be captured and removed from the patient after the surrounding and/or adjacent leaflet tissue has been cut.

Certain embodiments are directed to methods of cutting cardiac valve tissue at a targeted cardiac valve, such as a mitral valve. In some embodiments, a method includes positioning a delivery catheter within a body so that a distal end of the delivery catheter is positioned near the targeted cardiac valve, routing a cutting mechanism through the delivery catheter so that the cutting mechanism at least partially extends distally beyond the distal end of the catheter to enable the cutting mechanism to engage with leaflet tissue of the targeted cardiac valve, and actuating the cutting mechanism to cut at least one leaflet of the approximated adjacent leaflets.

In some implementations, the targeted cardiac valve is associated with an interventional implant (such as an interventional clip) that approximates adjacent leaflets of the targeted cardiac valve. Performance of the method therefore results in the cutting mechanism detaching the interventional implant from the at least one cut leaflet. Some methods include cutting all leaflets to which the interventional implant is attached. For example, both the anterior and the posterior leaflet of a mitral valve may be cut. The excised implant may then be removed from the patient (e.g., using a stabilizing cup).

In some embodiments, the targeted cardiac valve is a mitral valve, and the at least one cut leaflet is the anterior leaflet. In some implementations, the interventional device remains attached to the posterior leaflet. The targeted cardiac valve could also be the tricuspid, aortic, or pulmonic valve, for example.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 3A through 3F illustrate an embodiment of a cutting system including a cutting mechanism configured as a scissor like structure, showing various configurations of actuation mechanisms for controlling the cutting mechanism;

FIG. 4 illustrates an embodiment of a cutting system including a cutting mechanism configured as an electrically powered blade or needle structure;

FIG. 9 illustrates an embodiment of a cutting system including stabilizing prongs;

FIGS. 10A and 10B illustrate operation of the cutting system of FIG. 9, showing use of the stabilizing prongs in conjunction with a cutting mechanism to cut a valve leaflet.

DETAILED DESCRIPTION

Certain embodiments described herein are directed to interventional devices configured for cutting a cardiac valve, such as to enable removal of an implanted repair device from the cardiac valve and/or to prepare the site of the valve to subsequently receive a replacement cardiac valve or other implant. Certain embodiments are configured to route and/or deliver a cutting mechanism to a targeted cardiac valve through a transcatheter approach, such as a transfemoral, radial, or transjugular approach. Alternatively, other implementations can utilize a transapical approach for reaching the targeted cardiac valve.

Although many of the exemplary embodiments described herein are described in the context of cutting a mitral valve and releasing one or more interventional clip devices, it will be understood that similar principles may be applied to other implementations in which other implanted interventional devices are cut away from a mitral valve and/or in which one or more clips or other interventional devices are removed/cut away from another cardiac valve, such as the tricuspid valve. More generally, the exemplary embodiments described herein may be applied in other implementations involving removal of a previously implanted or deployed device from tissue.

Figure 1:
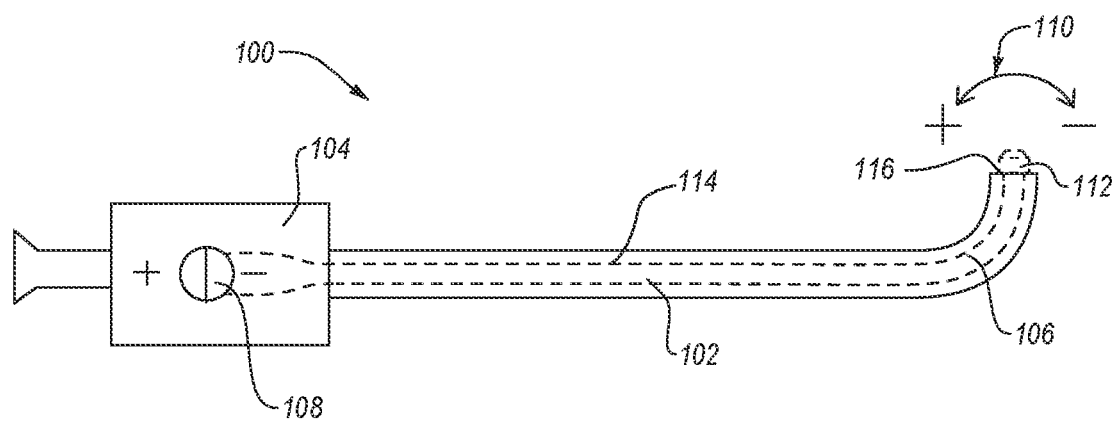
FIG. 1 illustrates an exemplary delivery system that may be utilized for guiding and/or delivering a cutting mechanism to a targeted cardiac valve.

FIG. 1 illustrates an exemplary embodiment of a delivery system 100 that may be utilized for routing a cutting mechanism to the targeted cardiac valve. The delivery system 100 includes a guide catheter 102 operatively coupled to a handle 104. The guide catheter 102 is configured to be steerable so as to enable guiding and orienting of the distal end 106 of the catheter. For example, the illustrated handle 104 includes a control 108 (e.g., dial, switch, slider, button, etc.) that can be actuated to control the curvature of the distal end 106 of the catheter 102, as indicated by arrows 110. As explained in more detail below with respect to other similar embodiments, the handle 104 can include one or more additional controls for actuating and/or adjusting one or more components of a cutting mechanism 112. The cutting mechanism 112 is illustrated generically in FIG. 1, and may represent any of the other cutting mechanism embodiments (along with corresponding controls and other associated components) described herein.

In some embodiments, the control 108 is operatively coupled to one or more control lines 114 (e.g., pull wires) extending from the handle 104 through the catheter 102 to the distal end 106 (e.g., through one or more lumens in the catheter 102). Actuation of the control 108 adjusts the tensioning of a control line 114 so as to pull the guide catheter 102 in the corresponding direction. The illustrated embodiment is shown as having a single control 108 for providing steerability in two opposing directions. Alternative embodiments may include additional controls (and associated control lines) for providing control in one or more additional directions.

The catheter 102 includes a lumen 116 through which the cutting mechanism 112 may be routed. Accordingly, the delivery system 100 may be utilized by positioning the distal end 106 near a targeted cardiac valve, and then routing the cutting mechanism 112 through the catheter 102 and out of the distal end 106 so as to position the cutting mechanism 112 at the targeted valve. Alternatively, a cutting mechanism 112 can be coupled to the distal end 106 so that it is positioned at the targeted valve as the distal end 106 reaches the targeted valve. As described previously, the delivery system 100 may be utilized in a transfemoral, transjugular, radial, or transapical approach, for example. The delivery system 100 may be utilized to guide any of the cutting mechanisms described herein, or equivalents thereof.

Figure 2A:
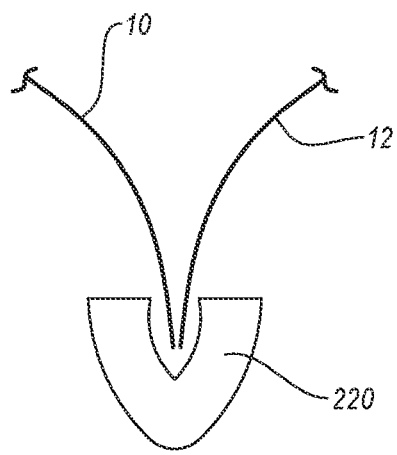
FIGS. 2A and 2B schematically illustrate a cross-sectional side view of a targeted mitral valve having an attached interventional clip device, showing cutting of one of the valve leaflets to effect detachment of the previously approximated leaflets.
Figure 2B:
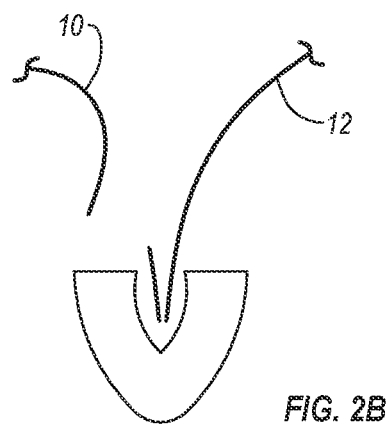

FIGS. 2A and 2B illustrate a targeted mitral valve having an attached interventional clip device 220, showing cutting of one of the valve leaflets (anterior leaflet 10) to effect detachment of the previously approximated leaflets. FIG. 2A illustrates the mitral valve and clip device 220 prior to leaflet cutting, and FIG. 2B illustrates the mitral valve and clip device 220 after leaflet cutting. One or more of the delivery system and/or cutting mechanism embodiments described herein may be utilized in such a procedure.

As shown, the clip device 220 is coupled to the anterior leaflet 10 and posterior leaflet 12. In many instances, an implant such as the clip device 220 will be embedded with the leaflet tissue and/or other surrounding tissues as a result of tissue ingrowth, making it difficult to extract the implant. As shown in FIG. 2B, one of the leaflets is cut (the anterior leaflet 10, in this example) in order to separate the leaflets. Such separation may be beneficial prior to deployment of a replacement valve, or to satisfy another clinical need to reverse or minimize the effects of the repair device 220. In one preferred implementation, the anterior leaflet 10 is cut so that the clip device 220 remains attached to the posterior leaflet 12. In this position, there is less risk that the clip device will interfere with functioning of the left ventricular outflow tract (LVOT).

In contrast, cutting the posterior leaflet 12 so that the clip device 220 remains on the anterior leaflet 10, can result in weighing down of the anterior leaflet 10, which in turn can lead to detrimental interference with the LVOT. However, certain applications may allow for leaving the clip device 220 on the anterior leaflet 10 with little or acceptable risk of LVOT interference and/or may involve subsequent removal/extraction of the clip device 220 from the anterior leaflet 10. Accordingly, methods in which a posterior valve is cut are also included within this disclosure.

FIG. 3A illustrates an embodiment of a cutting system having a cutting mechanism 312 that may be utilized to cut a targeted valve to unfix/detach previously approximated valve leaflets. In this embodiment, the cutting mechanism 312 is configured as a scissor-like mechanism having opposing blade cutting elements 315 for cutting tissue. In the illustrated embodiment, the cutting mechanism 312 extends through or is attached to a distal end of a catheter 302. The cutting mechanism 312 is operatively connected to a handle 304, and the handle 304 is configured to enable selective actuation of the cutting mechanism 312. For example, the handle 304 may include one or more controls 308, and at least one of such controls 308 may be operatively coupled to the cutting mechanism 312. The control 308 may be, for example, a button, switch, dial, slider, or other suitable actuation mechanism providing a user with selective control over the cutting mechanism 312.

As shown by arrow 313, the cutting system shown in FIG. 3A is also configured to allow rotational adjustment of the cutting mechanism 312 about a longitudinal axis that extends through the catheter 302. Rotational adjustment may be accomplished, for example, by rotating the handle 304, with the rotational torque from turning the handle 304 being transferred distally to the cutting mechanism 312. Additionally, or alternatively, the cutting mechanism 312 may be rotated relative to the handle 304 through actuation of a control 308 of the handle 304. The ability to rotate the cutting mechanism 312 beneficially allows an operator to properly orient the cutting mechanism 312 relative to a targeted cardiac valve or other targeted anatomy so that a desired cut may be made.

As shown in the expanded views of FIGS. 3B through 3E, the cutting mechanism 312 may be joined to one or more control lines 314 (e.g., passing through a lumen of the catheter 302) that control actuation of the cutting mechanism 312 through adjustments to the tension of the one or more control lines 314.

Figure 3B:
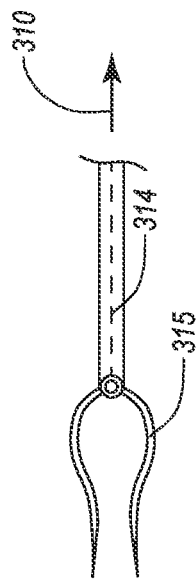
Figure 3C:
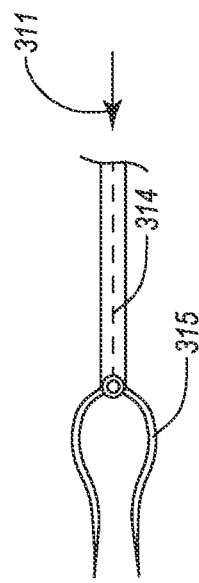

In one configuration, shown in FIGS. 3B and 3C, the opposing blades 315 are operatively coupled to the control line 314 such that adjusting tension (shown by arrows 310) of the control line 314 allows the blades 315 to move between the closed position shown in FIG. 3B and the open position shown in FIG. 3C. In this configuration, the application of tension to control line 314 moves the blades 315 to the open position and the release of tension moves the blades 315 to the closed position. The blades 315 may, for example, be biased toward the closed position shown in FIG. 3B. The blades 315 may be operated by applying tension to the control line 314 to move the blades 315 toward the open position shown in FIG. 3C, then releasing tension in the control line 314 to cause the blades 315 to close and provide a cutting motion.

Figure 3D:
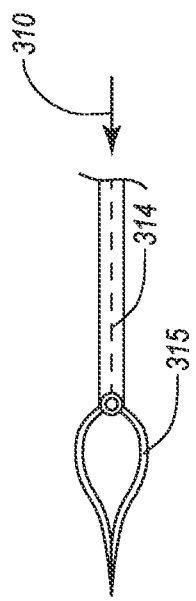
Figure 3E:
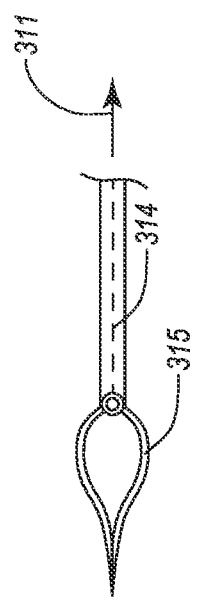

FIGS. 3D and 3E show another configuration in which the blades 315 close through the application of tension to the control line 314 and open upon release of tension (shown by arrows 311). The blades 315 may, for example, be biased toward the open position shown in FIG. 3E. The blades 315 may be operated by releasing tension to the control line 314 to move the blades 315 toward the open position shown in FIG. 3E, then reapplying tension in the control line 314 to cause the blades 315 to close and provide a cutting motion.

Figure 3F:
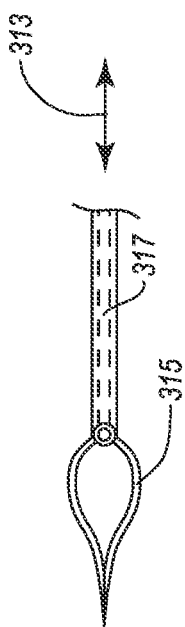

FIG. 3F illustrates another embodiment in which the cutting mechanism includes a control rod 317 operatively coupled to the cutting blades 315. Translation of the control rod 317 (shown by arrows 313) provides control over opening and closing of the blades 315. In some embodiments, distal translation of the control rod 317 causes the blades 315 to open while proximal translation of the control rod 317 causes the blades 315 to close. In other embodiments, distal translation of the control rod 317 causes the blades 315 to close while proximal translation of the control rod 317 causes the blades 315 to open. One or more push rods such as control rod 317 may be used in addition to or as an alternative to the one or more control lines 314 for controlling the cutting blades 315. The control elements and configurations shown in FIGS. 3A through 3E, including the control line(s) 314, the control rod(s) 317, and their mechanical and operational relationship with the cutting mechanism, may be utilized in any of the other embodiments described herein.

FIG. 4 illustrates another embodiment of a cutting system having a cutting mechanism 412 operatively coupled to a handle 404. In this embodiment, the cutting mechanism 412 is configured as a blade, needle, or other sharp member capable of cutting through cardiac valve leaflet tissue. The illustrated cutting mechanism 412 is further configured to provide an oscillating or translating motion to enable cutting of tissue against which the cutting mechanism 412 is engaged. As shown, the handle 404 includes a power source 417, such as a battery source or other source of electricity. Power may additionally or alternatively be provided by an external source such as through electrical cable 419 (e.g., AC or DC power). The cutting mechanism 412 is thereby powered to provide an oscillating, rotating, or other cutting motion through power transmission means known in the art. For example, the cutting mechanism 412 can include or can be operatively coupled to one or more motors 421 (e.g., servomotors) or other means of converting the delivered electrical power into the mechanical work of actuating the cutting mechanism 412.

As illustrated, motor 421 can be associated with the handle 404 and connected to linkage(s) 423 extending to the cutting mechanism 412 and thereby mechanically coupling the motor 421 to the cutting mechanism 412. The motor 421 can transfer, through the linkage(s) 423, rotative (as shown by arrow 413) and/or longitudinally oscillating (as shown by arrow 410) motion. This motion powers the cutting mechanism 412 and allows it to cut through targeted cardiac tissue or other targeted tissue.

Figure 5A:
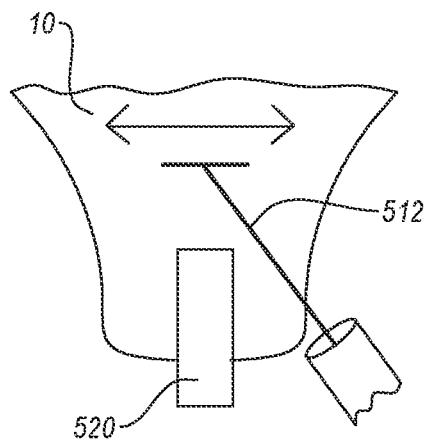
FIGS. 5A and 5B illustrate a superior view of deployment of a blade mechanism to cut a targeted valve leaflet to disengage a clip device from the remainder of the leaflet.
Figure 5C:
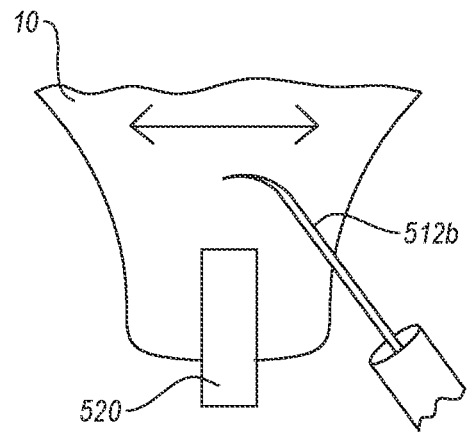
FIGS. 5C and 5D illustrate a superior view of deployment of a needle mechanism to cut a targeted valve leaflet to disengage a clip device from the remainder of the leaflet.
Figure 5B:
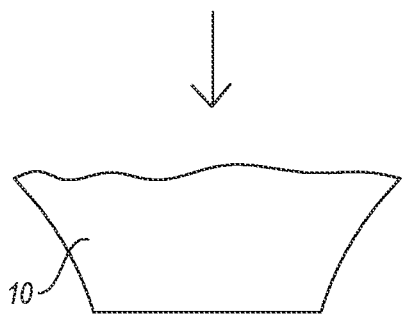
Figure 5D:
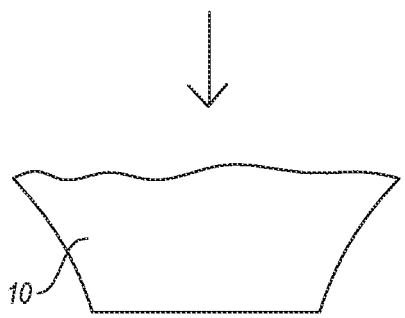

FIGS. 5A and 5B illustrate cutting of an anterior leaflet 10 to detach a clip device 520 from the anterior leaflet 10 using a cutting mechanism 512 having a blade structure, and FIGS. 5C and 5D illustrate a cutting procedure accomplished using a cutting mechanism 512b having a needle structure.

Figure 6:
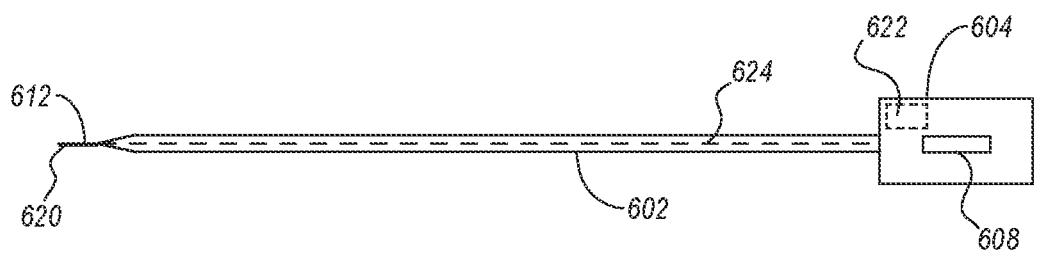
FIG. 6 illustrates an embodiment of a cutting system including a cutting mechanism configured to cut using RF energy.

FIG. 6 illustrates another embodiment of a cutting system including a cutting mechanism 612 operatively coupled to a handle 604. In this embodiment, the cutting mechanism includes a tip 620 capable of transmitting radio frequency (RF) energy to the targeted valve leaflets in order to provide tissue cutting functionality. The tip 620 may be configured as a blade, needle, or other relatively sharp component; however, the tip structure need not necessarily be inherently sharp enough to cut targeted tissue in applications in which RF electrical current is used to provide the cutting functionality.

The illustrated handle 604 includes an RF energy source 622. The RF energy from the RF energy source 622 may be transmitted distally along the length of the catheter 602 to the tip 620 of the cutting mechanism 612. For example, the RF energy may be transmitted through a conductor 624, which may be formed as a metallic cable or other structure suitable for transmitting RF energy. The handle 604 also includes a control 608 configured to enable control of the cutting mechanism 612 and/or adjustment to the RF energy source 622 and the applied RF energy.

In an alternative embodiment, the tip 620 of the cutting mechanism 612 is configured as a heat-transmitting structure capable of transmitting sufficient thermal energy (not induced using RF electrical current) to the targeted valve tissue to ablate and cut the valve tissue. In such embodiments, the cutting mechanism 612 is thermally coupled to a source of thermal energy at the handle 604, and the thermal energy is transmitted through the length of the catheter 602 (e.g., through conductor 624) and sufficiently concentrated at the tip 620 of the cutting mechanism 612 to provide tissue cutting functionality.

Figure 7A:
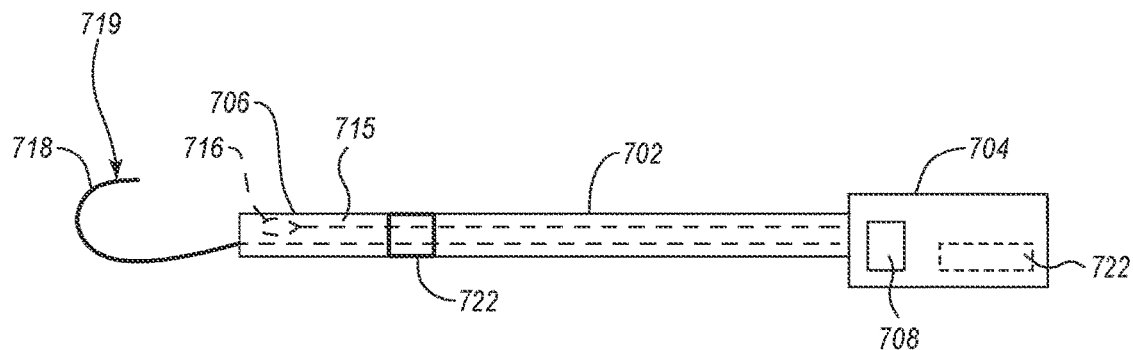
FIGS. 7A through 7D illustrate an embodiment of a cutting system including a cutting mechanism configured to form a noose structure for tightening around a targeted valve leaflet to cut the leaflet.
Figure 7B:
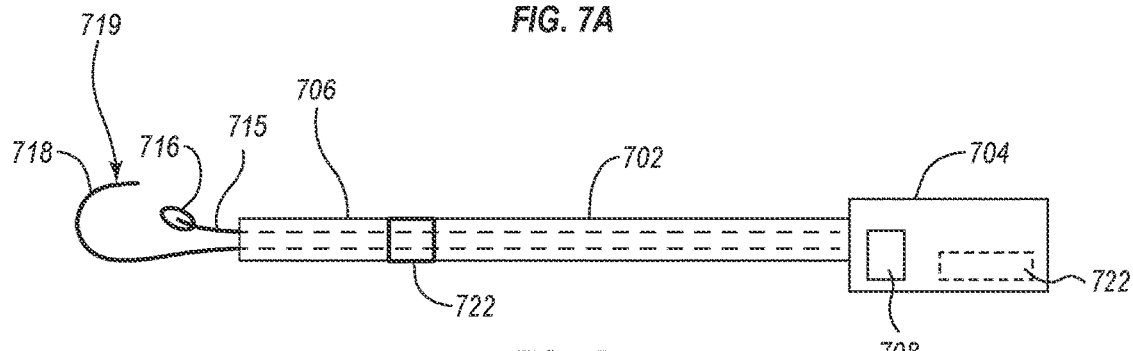
Figure 7C:
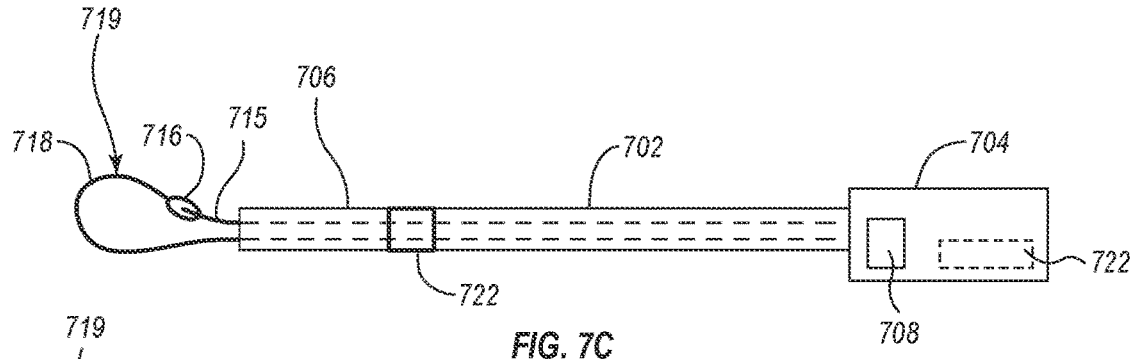

FIGS. 7A through 7C illustrate another embodiment of a cutting system that may be utilized in a valve cutting procedure. In this embodiment, the cutting mechanism is configured as a noose structure 719 for wrapping around a targeted valve leaflet to enable cutting of the leaflet upon tightening of the noose structure. As shown, the cutting system includes a handle 704 and a catheter 702 extending distally from the handle 704 to a distal end 706. As shown by the progressive succession from FIG. 7A to FIG. 7C, the noose structure 719 includes a snare 716 (including a distal loop and a wire 715 extending proximally therefrom) and a wire 718 (including a hook at its distal end) that is passable through the snare 716 to form the closed noose structure 719.

The illustrated cutting system may also include a collet 722 through which both the first wire 715 and the second wire 718 pass. The collet 722 may be configured to lock onto the wires 715 and 718 and may be translatable with respect to the catheter 702. In this manner, the diameter of the exposed portion of the noose structure 719 may be adjusted by translating the collet 722 after the collet 722 has been locked to the wires 715 and 718. For example, the diameter of the noose structure 719 may be enlarged by pushing the collet 722 distally to move more of the wires 715 and 718 distally beyond the catheter 702, and may be reduced by retracting the collet 722 proximally to pull more of the wires 715 and 718 within the catheter 702.

Although the illustrated collet 722 is shown as being disposed within the catheter 702, alternative embodiments position the collet 722 further proximally, such as at the handle 704. In some embodiments, the collet 722 and/or wires 715, 718 may be operatively coupled to a control 708 disposed at the handle 704, with the wires 715 and 718 extending proximally to the control 708 at the handle 704. As with other embodiments described herein, the control 708 may be configured as a button.

Figure 7D:
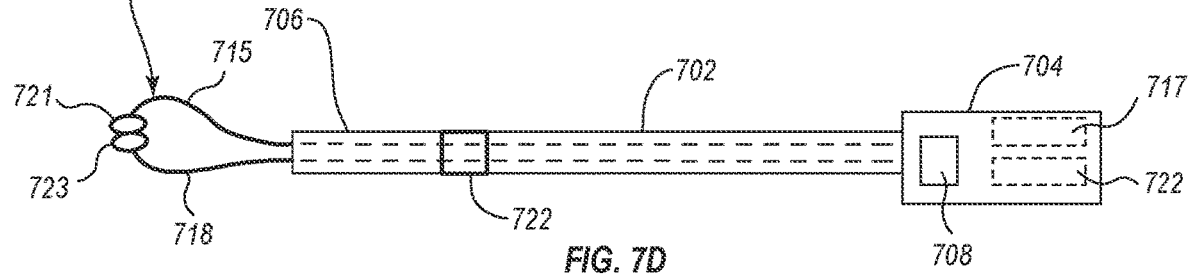

FIG. 7D illustrates an alternative configuration in which the noose structure 719 includes a first magnet 721 and second magnet 723 attached at the distal ends of respective wires 715 and 718. The magnets 721 and 723 may independently be electromagnets (e.g., powered by power source 717) or permanent magnets. The magnets 721 and 723 are configured to attract and magnetically couple to one another to form the noose structure 719.

Figure 8A:
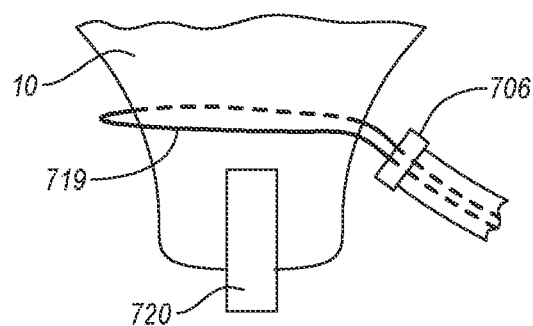
FIGS. 8A and 8B illustrates operation of the cutting system of FIGS. 7A through 7D, showing formation of the noose structure and cutting of a valve leaflet.
Figure 8B:
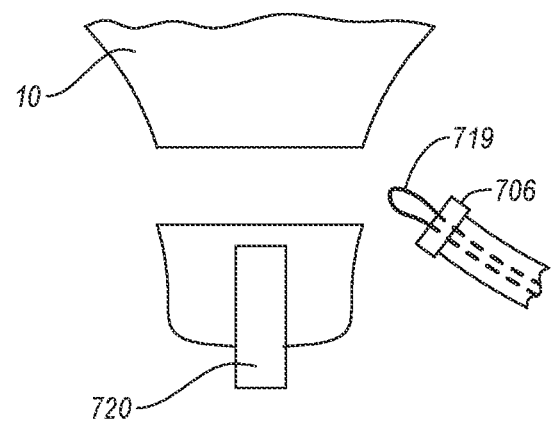

FIGS. 8A and 8B illustrate use of the noose structure 719 shown in FIGS. 7A through 7D to cut a targeted cardiac valve leaflet 10. As shown in FIG. 8A, the noose structure 719 may first be positioned around the targeted leaflet 10. This may be accomplished by positioning the distal end 706 of the catheter 702 near the targeted leaflet 10, and then forming the noose structure 719 around the leaflet 10 by extending the wires 715 and 718 (see FIGS. 7A through 7D) around opposite sides of the leaflet 10. After the noose structure 719 has been formed around the targeted leaflet 10, the leaflet may be cut by mechanically tightening the noose structure 719 such that the noose structure 719 cuts into the tissue. Alternatively, the leaflet 10 may be cut by tightening the noose structure 719 to bring it into contact with the targeted leaflet 10 and then applying radio frequency electrical and/or thermal energy to the noose structure 719 (e.g., using RF and/or thermal energy source 722 as shown in FIGS. 7A through 7D). In FIG. 8B, the leaflet 10 is shown having been cut so as to separate the clip device 720 from the leaflet.

FIG. 9 illustrates an embodiment of a cutting system that includes a plurality of stability components which may be utilized to engage with or against tissue at or near the targeted valve. The stabilizing prongs 824 and associated components may be included in other cutting system embodiments described herein, including the embodiments shown in FIG. 1 and FIGS. 3A through 8B.

In the illustrated embodiment, a pair of prongs 824 extend distally from a distal end 806 of the catheter 802 along with the cutting mechanism 812. Other embodiments may include a different number of prongs (e.g., three, four, or more). Similar to other embodiments described above, the cutting mechanism 812 may be controlled using one or more control elements operatively coupled to the cutting mechanism 812 and to a control 808 of the handle 804. As with the cutting mechanism 812, the prongs 824 may be controllable via one or more controls 809 of the handle 804, such as by adjusting the tension in one or more control lines 814 extending through the catheter 802 to the prongs 824, through the translation of an actuator rod or catheter relative to the prongs 824, and/or through another control mechanism that operatively connects the handle 804 to the prongs 824. In some embodiments, the prongs 824 may be replaced by or may be used in conjunction with a stabilizing cup (see FIGS. 11A through 13B).

The described stabilization components may be utilized in conjunction with one or more components of any of the other cutting mechanism embodiments described herein in order to stabilize the position of the distal end 806 of the catheter 802 relative to the targeted valve tissue. For example, FIG. 10A illustrates engagement of the prongs 824 against a targeted leaflet 10 to stabilize position of the blade 812 relative to the leaflet 10. The blade 812 and/or prongs 824 may then be actuated to move the blade 812 across the leaflet 10. FIG. 10B illustrates the cut leaflet and the separated clip device 820.

Embodiments described herein are described in the context of cutting leaflet tissue around a single deployed clip device, such as by cutting a single leaflet in a mitral valve (preferably the anterior leaflet). In other implementations, both leaflets may be cut so as to completely free the clip device. In such applications, prongs (such as the prongs 824 illustrated in FIG. 9) and/or a cup (such as the cup 926 or 1026 illustrated in FIGS. 11A through 13B) may be utilized to grasp the clip device as it is cut free. The extracted clip device may then be removed by retracting the prongs and/or cup through the catheter, carrying the extracted clip device away from the targeted valve. Additionally, or alternatively, a vacuum may be applied to the catheter (such as by applying suction at the proximal end and/or handle) to enable the extracted clip device to be pulled into the catheter and removed.

FIGS. 11A through 11D illustrates an embodiment of a cutting system having a catheter 902 extending distally from a handle (not shown; see, e.g., FIG. 1), a cutting mechanism 912 that extends through or is attached to a distal end of the catheter 902, and a stabilizing cup 926 capable of extending distally from the distal end of the catheter 902. The cutting mechanism 912 is shown here in generic form as a dashed line, and cutting mechanism 912 therefore represents any of the cutting mechanism embodiments described herein, including the noose structure 719 of FIGS. 7A through 8B, cutting mechanism 612 of FIG. 6, cutting mechanism 512 of FIG. 5A, cutting mechanism 512b of FIG. 5C, or cutting mechanism 312 of FIGS. 3A through 3F.

In the illustrated embodiment, the cup 926 is attached to an inner member 928 which extends proximally from the cup 926 toward the handle. By advancing or retracting the inner member 928 relative to the catheter 902, the cup 926 may be respectively advanced past the distal end of the catheter 902 or retracted into the catheter 902. The inner member 928 may be formed, for example, as a hypotube, push rod, catheter, or other suitable structure capable of transmitting longitudinal movement to the cup 926.

Figure 11A:
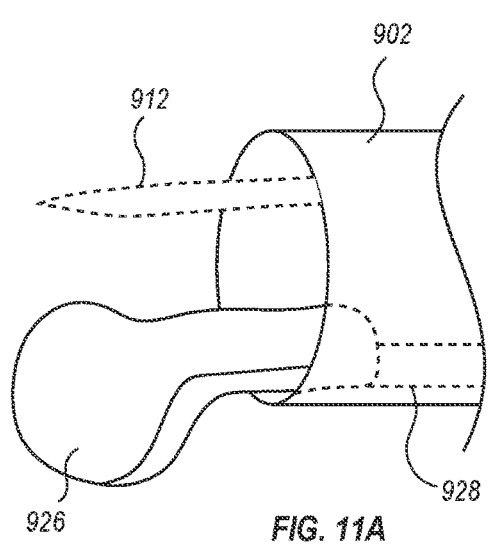
FIGS. 11A through 11D illustrate an embodiment of a cutting system including a stabilizing cup configured for stabilizing the cutting system with respect to a targeted cardiac valve and for receiving an excised interventional device.

The cup 926 may be formed as an expandable structure capable of moving between a collapsed, lower profile configuration and an expanded, fully open configuration. For example, the cup 926 may be biased toward the expanded, fully open position such that when the cup 926 is advanced past the distal end of the catheter 902 (and/or the catheter 902 is retracted to expose the cup 926) the cup 926 self-expands from the collapsed configuration to the open, expanded position. As shown in FIG. 11A, as the cup 926 is advanced relative to the catheter 902, the distal-most portion of the cup 926 begins to open and expand, while the more proximal portion remaining within the lumen of the catheter 902 remains in a collapsed configuration. In some embodiments, the cup 926 includes a frame structure made of a suitable self-expanding material, such as nitinol. The frame structure may also be covered in a membrane (e.g., formed from a suitable medical-grade polymer) to further define the shape of the cup 926.

Figure 11B:
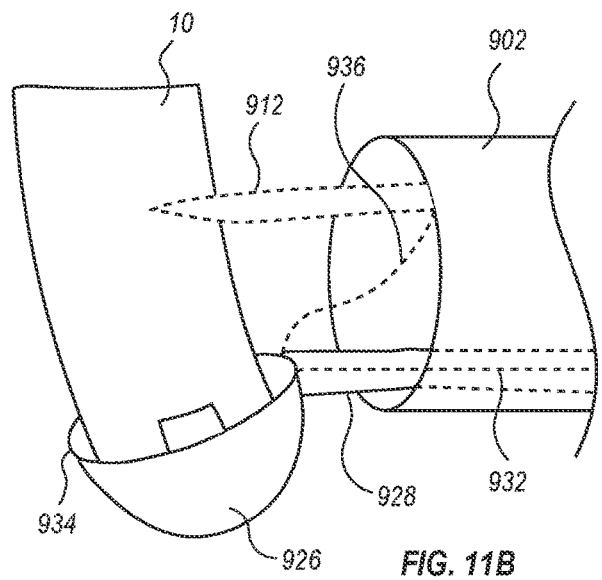

As shown in FIG. 11B, the cup 926 is configured to contact and cup the implanted interventional device 920 and/or leaflet tissue adjacent the implanted interventional device 920. In procedures where the interventional device 920 is completely cut free from the targeted cardiac valve 10 (e.g., where both leaflets of the mitral valve are cut), the cup 926 can function to hold and receive the excised interventional device 920. In the illustrated embodiment, the cup 926 is coupled to an adjustment wire 932 which extends proximally to the handle (e.g., through the inner member 928). The application and release of tension in the adjustment wire 932 causes the cup 926 to tighten and loosen, respectively, around the targeted valve 10. For example, the adjustment wire 932 may wrap around the periphery 934 of the cup 926 such that the application of tension to the adjustment wire 932 causes the periphery 934 of the cup 926 to "cinch" to a smaller diameter. For purposes of clarity, FIGS. 11B and 11C illustrate the cup 926 with a somewhat loose grasp to the targeted valve 10, it will be understood that the cup 926 may be adjusted to a desired fit or tightness against the targeted valve 10.

In preferred embodiments, the catheter 902 is a multi-lumen catheter including a lumen for the cutting mechanism 912 and a separate lumen for the cup 926 and inner member 928. Alternatively, the catheter 902 may be a single-lumen catheter. In such a single-lumen catheter embodiment, the cutting system may additionally include a tether 936 coupling the cup 926 to the cutting mechanism 912, as shown in FIG. 11B. For example, in a single-lumen catheter embodiment, the cup 926 may be deployed first, then detached from the inner member 928. The cutting mechanism 912 may then be deployed to cut the valve 10. The tether 936 maintains connection of the cutting system to the cup 926.

Figure 11C:
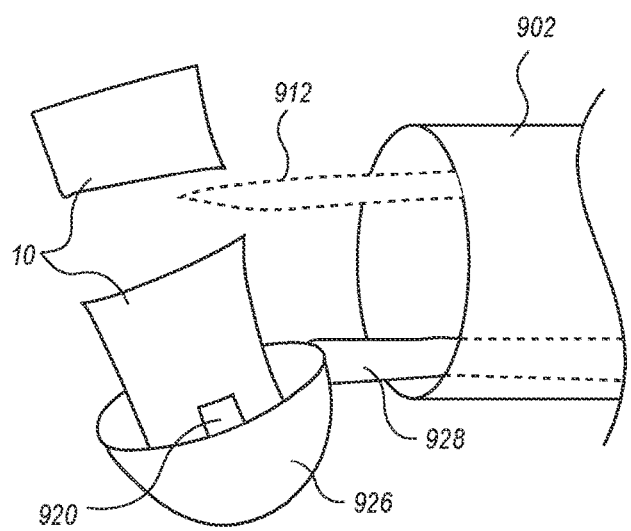
Figure 11D:
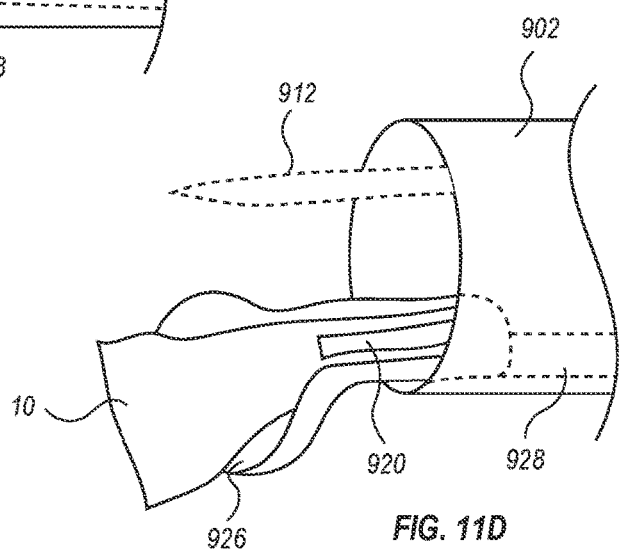

As shown in FIG. 11C, after the cutting mechanism 912 has cut the targeted valve 10, the cup 926 remains in contact with the cut portion of the leaflet tissue which includes the excised interventional device 920. As shown in FIG. 11D, the cup 926 may then be retracted into the catheter 902 to allow the excised interventional device 920 to be withdrawn from the patient. The cup 926 may be included with other cutting system embodiments described herein, including the embodiments shown in FIGS. 1 and 3A through 10B.

Figure 12A:
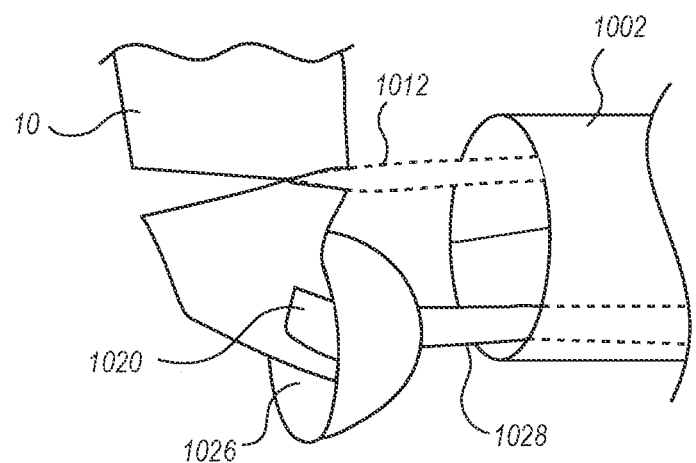
FIGS. 12A through 12C illustrate an embodiment of a cutting system including an alternative embodiment of a stabilizing cup.
Figure 12B:
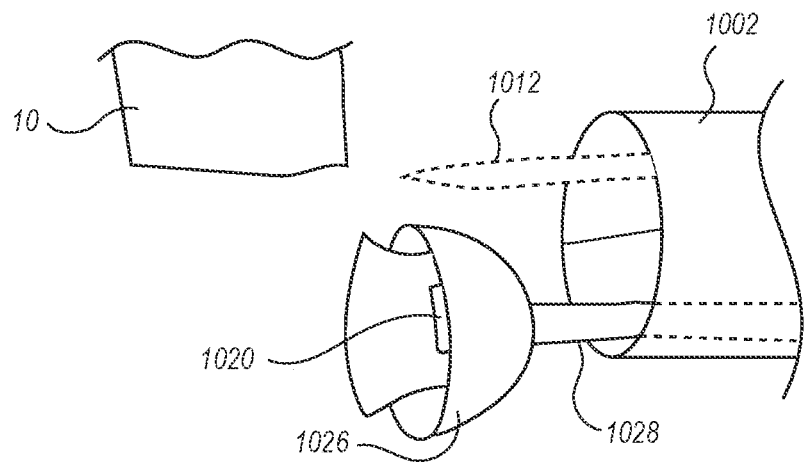
Figure 12C:
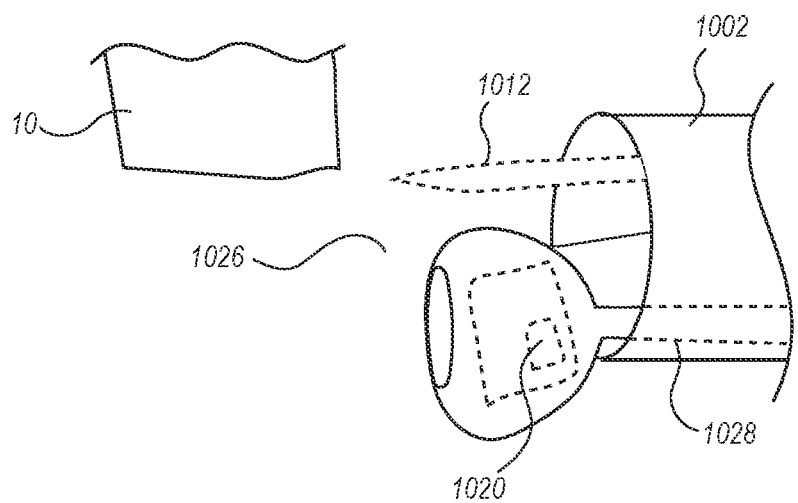

FIGS. 12A through 12C illustrate an alternative embodiment of a cutting system including a catheter 1002 (shown here as a multi-lumen catheter), cutting mechanism 1012, inner member 1028, and cup 1026. The cutting system shown in FIGS. 12A through 12C may be configured similar to the cutting system of FIGS. 11A through 11D. However, whereas the cup 926 is oriented to open in a direction transverse to the longitudinal axis of the catheter 902, the cup 1026 is oriented to open in a direction substantially aligned with the longitudinal axis of the catheter 1002. FIG. 12A illustrates that the interventional device 1020 and surrounding tissue is grasped within the cup 1026 as the valve 10 is cut by the cutting mechanism 1012, FIG. 12B illustrates the excised interventional device 1020 held within the cup 1026 after the valve 10 has been cut, and FIG. 12C illustrates tightening and/or "cinching" of the cup 1026 to more fully hold the excised interventional device 1020. After receiving the excised interventional device 1020, the cup 1026 may be retracted into the catheter 1002 and the system removed from the patient.

Figure 13A:
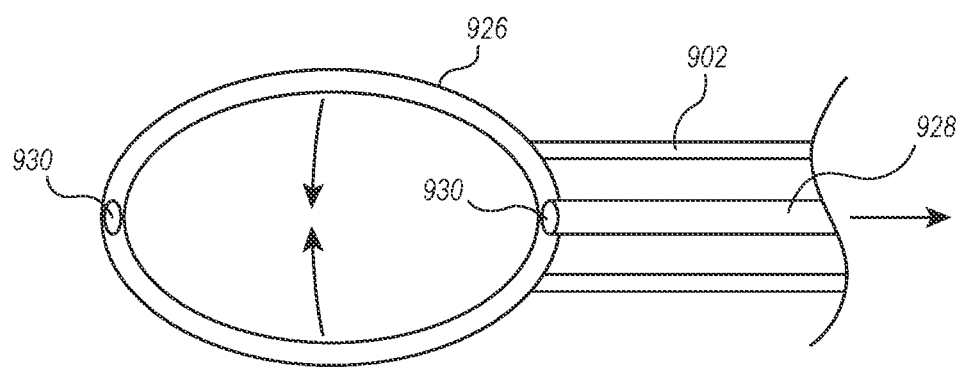
FIGS. 13A and 13B illustrate cup closing mechanisms for cup embodiments having self-expanding properties.
Figure 13B:
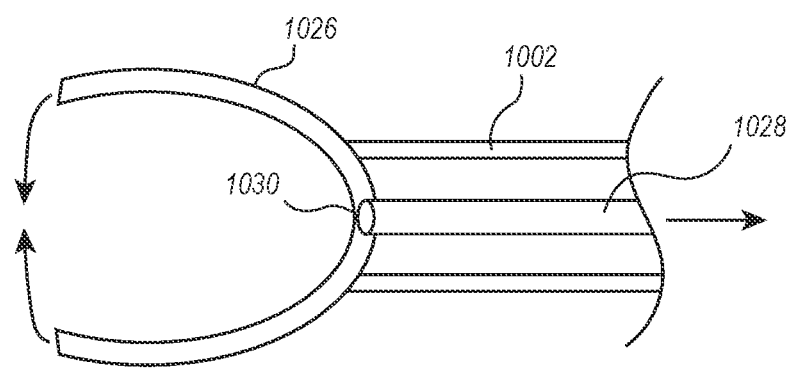

FIGS. 13A and 13B further illustrate closing mechanics related to the cup 926 of FIGS. 11A through 11D and the cup 1026 of FIGS. 12A through 12C, respectively. FIG. 13A illustrates a cross-sectional view of the distal portion of the catheter 902, showing the opening/rim of the cup 926. As the inner member 928 is retracted relative to the catheter 902, the cup 926 is brought into contact against the distal end of the catheter 902. The peripheral curvature of the cup 926 at the point where the cup 926 abuts the catheter 902 allows the cup 926 to collapse into a more oblong and lower profile shape as it is forced against the distal end of the catheter 902. Further proximal retraction of the inner member 928 forces the cup 926 to a correspondingly lower profile until it can be retracted fully within the catheter 902. In the illustrated embodiment, the frame of the cup 926 may include one or more pivot points 930 that aid in folding of the cup 926 toward the collapsed position. Other embodiments may omit pivot points 930 and may instead utilize inherent flexibility of the frame to allow collapse of the cup 926.

FIG. 13B illustrates a cross-sectional view of the catheter 1002 and cup 1026. Similar to the embodiment of FIG. 13A, proximal retraction of the inner member 1028 relative to the catheter 1002 brings the cup 1026 into contact against the distal end of the catheter 1002. The peripheral curvature of the cup 1026 at the point where the cup 1026 contacts the catheter 1002 allows the distal rim of the cup 1026 to collapse radially inward as the cup 1026 is forced against the distal end of the catheter 1002.

The terms "approximately," "about," and "substantially" as used herein represent an amount or condition close to the stated amount or condition that still performs a desired function or achieves a desired result. For example, the terms "approximately," "about," and "substantially" may refer to an amount or condition that deviates by less than 10%, or by less than 5%, or by less than 1%, or by less than 0.1%, or by less than 0.01% from a stated amount or condition.

Elements described in relation to any embodiment depicted and/or described herein may be combinable with elements described in relation to any other embodiment depicted and/or described herein. For example, any element described in relation to the delivery system 100 of FIG. 1, the stabilizing prongs of FIG. 9, and/or the stabilizing cups of FIGS. 11A through 13B, may be combinable with any element described in relation to any of the cutting mechanisms of FIGS. 3A through 8B. Likewise, elements of the delivery system of FIG. 1 may be utilized in any of the other cutting system embodiments described herein, elements of the stabilizing prongs of FIG. 9 may be utilized in any of the other cutting system embodiments described herein, and elements of either of the stabilizing cups of FIGS. 11A through 13B may be utilized in any of the other cutting system embodiments described herein.

What is claimed is:

1. An interventional device for cutting tissue at a targeted cardiac valve, the interventional device comprising:
    a catheter having a proximal end and a distal end, the distal end of the catheter being positionable at the targeted cardiac valve;
    a cutting mechanism positionable at the distal end of the catheter, the cutting mechanism including a noose structure positionable around leaflet tissue of the targeted cardiac valve to enable cutting of the leaflet tissue;
    a handle coupled to the proximal end of the catheter, the handle including one or more cutting controls operatively coupled to the cutting mechanism to provide selective actuation of the cutting mechanism; and
    a collet operatively coupled to the noose structure, the collet being longitudinally translatable within the catheter to enable selective adjustment of size of the noose structure,
    wherein the cutting mechanism includes a first wire and a second wire, a first magnet being coupled to a distal end of the first wire and a second magnet being coupled to a distal end of the second wire, the first and second magnets being configured to couple with one another to form the noose structure.

2. The interventional device of claim 1, wherein the noose structure is configured to be selectively adjusted in diameter to enable tightening of the noose structure around the leaflet tissue.

3. The interventional device of claim 1, wherein the noose structure is configured to provide radio frequency electrical current and/or thermal energy to the targeted valve to enable cutting of the leaflet tissue.

4. The interventional device of claim 1, wherein the cutting mechanism includes a hook and a snare, the snare being configured to engage with the hook to form the noose structure, wherein one or both of the hook and the snare are translatable relative to the distal end of the catheter.

5. The interventional device of claim 4, wherein the snare is coupled to a first wire and the hook is coupled to a second wire, the first and second wires extending proximally through the catheter to the handle.

6. A method of cutting cardiac valve tissue at a targeted cardiac valve within a body, the method comprising:

positioning a catheter within a body so that a distal end of the catheter is positioned near the targeted cardiac valve and an interventional implant that approximates adjacent leaflets of the targeted cardiac valve, the catheter having a distal end that is positionable at the targeted cardiac valve;

extending a cutting mechanism at least partially distally beyond the distal end of the catheter to enable the cutting mechanism to engage with leaflet tissue of the targeted cardiac valve, the cutting mechanism comprising a noose structure positionable around leaflet tissue of the targeted cardiac valve to enable cutting of the leaflet tissue, the noose structure being operatively coupled to one or more cutting controls disposed at a handle, the cutting mechanism includes a first wire and a second wire, a first magnet being coupled to a distal end of the first wire and a second magnet being coupled to a distal end of the second wire, the first and second magnets being configured to couple with one another to form the noose structure, the handle is coupled to the proximal end of the catheter and includes one or more cutting controls operatively coupled to the cutting mechanism to provide selective actuation of the cutting mechanism, and a collet is operatively coupled to the noose structure and is longitudinally translatable within the catheter to enable selective adjustment of size of the noose structure; and actuating the cutting mechanism to cut at least one leaflet of the approximated adjacent leaflets, the cutting mechanism thereby detaching the interventional implant from the at least one cut leaflet.

7. The method of claim 6, wherein the targeted cardiac valve is a mitral valve having an anterior leaflet and a posterior leaflet.

8. The method of claim 7, wherein the at least one cut leaflet is the anterior leaflet, the interventional implant remaining attached to the posterior leaflet.

9. The method of claim 7, wherein both the anterior leaflet and the posterior leaflet are cut, the method further comprising removing the interventional implant from the body after it is extracted from the mitral valve.

10. The method of claim 6, wherein the interventional implant is an interventional clip previously implanted at the mitral valve.

* * * * *